United States Patent
McAuley et al.

(10) Patent No.: US 12,390,610 B2
(45) Date of Patent: *Aug. 19, 2025

(54) BREATHING ASSISTANCE APPARATUS

(71) Applicant: Fisher & Paykel Healthcare Limited, Auckland (NZ)

(72) Inventors: Alastair Edwin McAuley, Dallas, TX (US); Gregory James Olsen, Auckland (NZ); Roheet Patel, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 26 days.

This patent is subject to a terminal disclaimer.

(21) Appl. No.: 18/468,663

(22) Filed: Sep. 15, 2023

(65) Prior Publication Data

US 2024/0115827 A1     Apr. 11, 2024

Related U.S. Application Data

(60) Continuation of application No. 17/816,275, filed on Jul. 29, 2022, now Pat. No. 11,766,535, which is a
(Continued)

(51) Int. Cl.
*A61M 16/06* (2006.01)
*A61M 16/00* (2006.01)
(Continued)

(52) U.S. Cl.
CPC .... *A61M 16/0622* (2014.02); *A61M 16/0066* (2013.01); *A61M 16/0616* (2014.02);
(Continued)

(58) Field of Classification Search
CPC .............. A61M 16/06; A61M 16/0605; A61M 16/0611; A61M 16/0616; A61M 16/0622;
(Continued)

(56) References Cited

U.S. PATENT DOCUMENTS

| 301,111 A | 7/1884 | Genese |
| 472,238 A | 4/1892 | Van Orden |
| (Continued) | | |

FOREIGN PATENT DOCUMENTS

| AU | 2009321054 | 7/2015 |
| CA | 1311662 | 12/1992 |
| (Continued) | | |

OTHER PUBLICATIONS

Opponent's outline of submissions in the matter of Australian patent applications Nos. 20223628, 2021201838, 2021201840, 2021201841, 2021201842 and 2021201843, dated Mar. 13, 2024, 51 pp.
(Continued)

*Primary Examiner* — Joseph D. Boecker
(74) *Attorney, Agent, or Firm* — VIA LLP

(57) ABSTRACT

A mask assembly for use as part of an apparatus for supplying a flow of respiratory gases to a user is disclosed. The mask assembly includes a mask body having an inlet through which said flow of respiratory gases are provided to the interior of said mask body. A mask seal assembly comprising a seal of flexible material and a clip of rigid material is attached to the body. The seal has a first side and a second side. The first side of the seal is shaped to approximately match the contours of a user's face and in use substantially seal against a user's face. The second side is attached to the clip. The clip provides an interface extending substantially the full perimeter or periphery of the mask seal assembly for releasably attaching the mask seal assembly to the mask body. The clip comprises a bridging portion spanning outwards from the perimeter or periphery of the mask body to space at least a portion of the second side of the seal outwards from the perimeter or periphery of the mask body.

25 Claims, 15 Drawing Sheets

Related U.S. Application Data continuation of application No. 17/568,186, filed on Jan. 4, 2022, now Pat. No. 11,559,650, which is a continuation of application No. 16/384,218, filed on Apr. 15, 2019, now Pat. No. 11,247,013, which is a continuation of application No. 15/425,937, filed on Feb. 6, 2017, now Pat. No. 10,835,702, and a continuation of application No. 14/977,083, filed on Dec. 21, 2015, now Pat. No. 10,272,218, said application No. 15/425,937 is a division of application No. 13/877,903, filed as application No. PCT/NZ2011/000211 on Oct. 7, 2011, now Pat. No. 9,561,338, said application No. 14/977,083 is a continuation of application No. 13/877,903, filed as application No. PCT/NZ2011/000211 on Oct. 7, 2011, now Pat. No. 9,561,338.

(60) Provisional application No. 61/391,527, filed on Oct. 8, 2010.

(51) Int. Cl.
*A61M 16/10* (2006.01)
*A61M 16/16* (2006.01)

(52) U.S. Cl.
CPC .... *A61M 16/0633* (2014.02); *A61M 16/0683* (2013.01); *A61M 2016/0039* (2013.01); *A61M 16/0069* (2014.02); *A61M 16/024* (2017.08); *A61M 16/109* (2014.02); *A61M 16/16* (2013.01); *A61M 2205/3368* (2013.01); *A61M 2205/50* (2013.01)

(58) Field of Classification Search
CPC .. A61M 16/0627; A62B 18/02; A62B 18/025; A62B 18/04; A62B 18/06
See application file for complete search history.

(56) References Cited

U.S. PATENT DOCUMENTS

| | | |
|---|---|---|
| 577,926 A | 3/1897 | Miller |
| 718,470 A | 1/1903 | Jones |
| 751,091 A | 2/1904 | Moran |
| 770,013 A | 9/1904 | Linn |
| 1,635,545 A | 7/1927 | Drager |
| 2,126,755 A | 8/1938 | Dreyfus |
| 2,228,218 A | 1/1941 | Schwartz |
| 2,241,535 A | 5/1941 | Boothby et al. |
| 2,296,150 A | 9/1942 | Dockson et al. |
| 2,353,643 A | 7/1944 | Bulbulian |
| 2,359,506 A | 10/1944 | Battley et al. |
| 2,388,604 A | 11/1945 | Eisenbud |
| 2,415,846 A | 2/1947 | Francis |
| 2,452,845 A | 11/1948 | Fisher |
| 2,508,050 A | 5/1950 | Valente |
| 2,684,066 A | 7/1954 | Glidden |
| 2,693,800 A | 11/1954 | Caldwell |
| 2,738,788 A | 3/1956 | Matheson et al. |
| 2,749,910 A | 6/1956 | Faulconer |
| 2,837,090 A | 6/1958 | Bloom |
| 2,843,121 A | 7/1958 | Hudson |
| 2,859,748 A | 11/1958 | Hudson |
| 2,875,759 A | 3/1959 | Galleher |
| 2,894,506 A | 7/1959 | Rose |
| 2,939,458 A | 6/1960 | Lundquist |
| 3,234,940 A | 2/1966 | Morton |
| 3,330,273 A | 7/1967 | Ray |
| 3,424,633 A | 1/1969 | Corrigall et al. |
| 3,490,452 A | 1/1970 | Greenfield |
| 3,545,437 A | 12/1970 | Quackenbush |
| 3,599,635 A | 8/1971 | Kenneth |
| 3,682,171 A | 8/1972 | Dali et al. |
| 3,834,682 A | 9/1974 | McPhee |
| 3,850,171 A | 11/1974 | Ball et al. |
| 3,894,562 A | 7/1975 | Mosley et al. |
| 3,972,321 A | 8/1976 | Proctor |
| 3,977,432 A | 8/1976 | Vidal |
| 3,982,532 A | 9/1976 | Halldin et al. |
| 3,992,720 A | 11/1976 | Nicolinas |
| 4,090,510 A | 5/1978 | Segersten |
| D250,047 S | 10/1978 | Lewis et al. |
| D250,131 S | 10/1978 | Lewis et al. |
| 4,127,130 A | 11/1978 | Naysmith |
| 4,150,464 A | 4/1979 | Tracy |
| D252,322 S | 7/1979 | Johnson |
| 4,201,205 A | 5/1980 | Bartholomew |
| 4,258,710 A | 3/1981 | Reber |
| 4,266,540 A | 5/1981 | Panzik et al. |
| 4,278,082 A | 7/1981 | Blackmer |
| 4,354,488 A | 10/1982 | Bartos |
| 4,367,735 A | 1/1983 | Dali |
| 4,378,011 A | 3/1983 | Warncke et al. |
| 4,437,462 A | 3/1984 | Piljay |
| 4,454,880 A | 6/1984 | Muto et al. |
| 4,574,799 A | 3/1986 | Warncke et al. |
| 4,603,602 A | 8/1986 | Montesi |
| 4,621,632 A | 11/1986 | Bartels et al. |
| 4,644,974 A | 2/1987 | Zingg |
| 4,676,241 A | 6/1987 | Webb et al. |
| 4,677,977 A | 7/1987 | Wilcox |
| D293,613 S | 1/1988 | Wingler |
| 4,753,233 A | 6/1988 | Grimes |
| 4,773,411 A | 9/1988 | Downs |
| 4,782,832 A | 11/1988 | Trimble et al. |
| 4,803,981 A | 2/1989 | Vickery |
| 4,804,160 A | 2/1989 | Harbeke |
| 4,836,200 A | 6/1989 | Clark et al. |
| 4,856,508 A | 8/1989 | Tayebi |
| 4,907,584 A | 3/1990 | McGinnis |
| 4,915,104 A | 4/1990 | Marcy |
| 4,915,105 A | 4/1990 | Lee |
| 4,919,128 A | 4/1990 | Kopala et al. |
| 4,938,209 A | 7/1990 | Fry |
| 4,941,467 A | 7/1990 | Takata |
| 4,944,310 A | 7/1990 | Sullivan |
| D310,431 S | 9/1990 | Bellm |
| 4,958,658 A | 9/1990 | Zajac |
| 4,971,051 A | 11/1990 | Toffolon |
| 4,986,269 A | 1/1991 | Hakkinen |
| 5,010,925 A | 4/1991 | Atkinson et al. |
| 5,016,625 A | 5/1991 | Hsu et al. |
| 5,031,261 A | 7/1991 | Fenner |
| 5,042,478 A | 8/1991 | Kopala et al. |
| 5,046,491 A | 9/1991 | Derrick |
| D320,677 S | 10/1991 | Kumagai et al. |
| D321,419 S | 11/1991 | Wallace |
| 5,062,421 A | 11/1991 | Burns et al. |
| 5,065,756 A | 11/1991 | Rapoport |
| D322,318 S | 12/1991 | Sullivan et al. |
| 5,074,297 A | 12/1991 | Venegas |
| 5,094,236 A | 3/1992 | Tayebi |
| 5,113,857 A | 5/1992 | Dickerman et al. |
| 5,121,745 A | 6/1992 | Israel et al. |
| 5,148,802 A | 9/1992 | Sanders et al. |
| 5,164,652 A | 11/1992 | Johnson et al. |
| 5,231,979 A | 8/1993 | Rose |
| 5,243,971 A | 9/1993 | Sullivan et al. |
| 5,245,995 A | 9/1993 | Sullivan et al. |
| D340,317 S | 10/1993 | Cole |
| 5,259,377 A | 11/1993 | Schroeder |
| 5,267,556 A | 12/1993 | Feng |
| 5,269,296 A | 12/1993 | Landis et al. |
| 5,315,859 A | 5/1994 | Schommer |
| 5,349,949 A | 9/1994 | Schegerin |
| 5,353,789 A | 10/1994 | Schobohm |
| 5,366,805 A | 11/1994 | Fujiki et al. |
| D354,128 S | 1/1995 | Rinehart |
| D355,484 S | 2/1995 | Rinehart |
| 5,400,776 A | 3/1995 | Bartholomew |
| 5,429,683 A | 7/1995 | Le Mitouard |
| 5,438,979 A | 8/1995 | Johnson et al. |

(56) References Cited

U.S. PATENT DOCUMENTS

| | | |
|---|---|---|
| 5,441,046 A | 8/1995 | Starr et al. |
| 5,449,206 A | 9/1995 | Lockwood |
| 5,449,234 A | 9/1995 | Gipp et al. |
| 5,458,202 A | 10/1995 | Fellows et al. |
| 5,460,174 A | 10/1995 | Chang |
| 5,461,932 A | 10/1995 | Hall |
| 5,477,852 A | 12/1995 | Landis et al. |
| 5,513,634 A | 5/1996 | Jackson |
| 5,518,802 A | 5/1996 | Colvin et al. |
| 5,533,506 A | 7/1996 | Wood |
| 5,540,223 A | 7/1996 | Starr et al. |
| 5,542,128 A | 8/1996 | Lomas |
| 5,551,419 A | 9/1996 | Froehlich et al. |
| 5,558,090 A | 9/1996 | James |
| 5,560,354 A | 10/1996 | Berthon-Jones et al. |
| 5,570,689 A | 11/1996 | Starr et al. |
| 5,588,423 A | 12/1996 | Smith |
| 5,595,174 A | 1/1997 | Gwaltney |
| 5,601,078 A | 2/1997 | Schaller et al. |
| D378,610 S | 3/1997 | Reischel et al. |
| 5,649,532 A | 7/1997 | Griffiths |
| 5,657,752 A | 8/1997 | Landis et al. |
| 5,662,101 A | 9/1997 | Ogden et al. |
| 5,664,566 A | 9/1997 | Mcdonald et al. |
| 5,687,715 A | 11/1997 | Landis |
| 5,690,097 A | 11/1997 | Howard et al. |
| 5,724,677 A | 3/1998 | Bryant et al. |
| 5,724,965 A | 3/1998 | Handke et al. |
| 5,746,201 A | 5/1998 | Kidd |
| 5,752,510 A | 5/1998 | Goldstein |
| 5,755,578 A | 5/1998 | Contant et al. |
| 5,789,660 A | 8/1998 | Kofoed et al. |
| 5,806,727 A | 9/1998 | Joseph |
| 5,807,295 A | 9/1998 | Hutcheon et al. |
| 5,857,460 A | 1/1999 | Popitz |
| 5,884,624 A | 3/1999 | Barnett et al. |
| 5,904,278 A | 5/1999 | Barlow et al. |
| 5,918,598 A | 7/1999 | Belfer |
| 5,921,239 A | 7/1999 | McCall et al. |
| 5,924,420 A | 7/1999 | Reischel |
| 5,941,245 A | 8/1999 | Hannah et al. |
| 5,943,473 A | 8/1999 | Levine |
| 5,953,763 A | 9/1999 | Gouget |
| 5,966,745 A | 10/1999 | Schwartz et al. |
| 6,016,804 A | 1/2000 | Gleason et al. |
| 6,017,315 A | 1/2000 | Starr et al. |
| 6,019,101 A | 2/2000 | Cotner et al. |
| 6,021,528 A | 2/2000 | Jurga |
| 6,039,044 A | 3/2000 | Sullivan |
| 6,050,260 A | 4/2000 | Daniell et al. |
| 6,112,746 A | 9/2000 | Kwok et al. |
| 6,116,235 A | 9/2000 | Walters et al. |
| 6,119,693 A | 9/2000 | Kwok et al. |
| 6,119,694 A | 9/2000 | Correa et al. |
| 6,127,071 A | 10/2000 | Lu |
| 6,135,109 A | 10/2000 | Blasdell et al. |
| 6,135,432 A | 10/2000 | Hebblewhite et al. |
| 6,192,886 B1 | 2/2001 | Rudolph |
| D440,302 S | 4/2001 | Wolfe |
| 6,272,933 B1 | 8/2001 | Gradon et al. |
| 6,298,850 B1 | 10/2001 | Argraves |
| 6,302,105 B1 | 10/2001 | Wickham et al. |
| 6,341,606 B1 | 1/2002 | Bordewick et al. |
| 6,347,631 B1 | 2/2002 | Hansen et al. |
| 6,354,293 B1 | 3/2002 | Madison |
| D455,891 S | 4/2002 | Biedrzycki |
| 6,398,197 B1 | 6/2002 | Dickinson et al. |
| 6,412,487 B1 | 7/2002 | Gunaratnam et al. |
| 6,412,488 B1 | 7/2002 | Barnett |
| 6,418,928 B1 | 7/2002 | Bordewick et al. |
| 6,418,929 B1 | 7/2002 | Norfleet |
| 6,422,238 B1 | 7/2002 | Lithgow |
| 6,427,694 B1 | 8/2002 | Hecker et al. |
| 6,431,172 B1 | 8/2002 | Bordewick |
| 6,435,181 B1 | 8/2002 | Jones, Jr. et al. |
| 6,439,234 B1 | 8/2002 | Curti et al. |
| 6,457,473 B1 | 10/2002 | Brostrom et al. |
| 6,467,483 B1 | 10/2002 | Kopacko et al. |
| 6,470,886 B1 | 10/2002 | Jestrabek-Hart |
| 6,478,026 B1 | 11/2002 | Wood |
| 6,484,725 B1 | 11/2002 | Chi et al. |
| 6,488,664 B1 | 12/2002 | Solomon et al. |
| 6,491,034 B1 | 12/2002 | Gunaratnam et al. |
| 6,497,232 B2 | 12/2002 | Fecteau |
| 6,513,526 B2 | 2/2003 | Kwok et al. |
| 6,526,978 B2 | 3/2003 | Dominguez |
| 6,530,373 B1 | 3/2003 | Patron et al. |
| 6,561,188 B1 | 5/2003 | Ellis |
| 6,561,190 B1 | 5/2003 | Kwok |
| 6,561,191 B1 | 5/2003 | Kwok |
| 6,571,798 B1 | 6/2003 | Thornton |
| 6,581,594 B1 | 6/2003 | Drew et al. |
| 6,581,601 B2 | 6/2003 | Ziaee |
| 6,581,602 B2 | 6/2003 | Kwok et al. |
| 6,584,977 B1 | 7/2003 | Serowski |
| 6,588,424 B2 | 7/2003 | Bardel |
| 6,615,832 B1 | 9/2003 | Chen |
| 6,629,531 B2 | 10/2003 | Gleason et al. |
| 6,631,718 B1 | 10/2003 | Lovell |
| 6,634,358 B2 | 10/2003 | Kwok et al. |
| 6,637,434 B2 | 10/2003 | Noble |
| 6,644,315 B2 | 11/2003 | Ziaee |
| 6,651,658 B1 | 11/2003 | Hill et al. |
| 6,651,663 B2 | 11/2003 | Barnett et al. |
| 6,659,102 B1 | 12/2003 | Sico |
| 6,662,803 B2 | 12/2003 | Gradon et al. |
| 6,668,828 B1 | 12/2003 | Figley et al. |
| D485,905 S | 1/2004 | Moore |
| 6,679,257 B1 | 1/2004 | Robertson et al. |
| 6,679,265 B2 | 1/2004 | Strickland et al. |
| 6,691,707 B1 | 2/2004 | Gunaratnam et al. |
| 6,712,072 B1 | 3/2004 | Lang |
| 6,736,139 B1 | 5/2004 | Wix |
| 6,769,432 B1 | 8/2004 | Keifer |
| 6,772,760 B2 | 8/2004 | Frater et al. |
| 6,772,761 B1 | 8/2004 | Rucker, Jr. |
| 6,796,308 B2 | 9/2004 | Gunaratnam et al. |
| 6,817,362 B2 | 11/2004 | Gelinas et al. |
| 6,823,869 B2 | 11/2004 | Raje et al. |
| 6,851,425 B2 | 2/2005 | Jaffre et al. |
| 6,851,428 B2 | 2/2005 | Dennis |
| 6,883,177 B1 | 4/2005 | Ouellette et al. |
| 6,892,729 B2 | 5/2005 | Smith et al. |
| 6,895,965 B2 | 5/2005 | Scarberry et al. |
| 6,907,882 B2 | 6/2005 | Ging et al. |
| 6,918,390 B2 | 7/2005 | Lithgow et al. |
| 6,951,218 B2 | 10/2005 | Gradon et al. |
| 6,953,354 B2 | 10/2005 | Edirisuriya et al. |
| 6,997,187 B2 | 2/2006 | Wood et al. |
| 7,004,165 B1 | 2/2006 | Salcido |
| 7,007,696 B2 | 3/2006 | Palkon et al. |
| 7,021,311 B2 | 4/2006 | Gunaratnam et al. |
| D520,140 S | 5/2006 | Chaggares |
| 7,051,765 B1 | 5/2006 | Kelley et al. |
| 7,066,179 B2 | 6/2006 | Eaton et al. |
| 7,077,126 B2 | 7/2006 | Kummer et al. |
| D526,094 S | 8/2006 | Chen |
| 7,096,864 B1 | 8/2006 | Mayer et al. |
| D533,269 S | 12/2006 | McAuley et al. |
| 7,178,525 B2 | 2/2007 | Matula, Jr. et al. |
| 7,178,528 B2 | 2/2007 | Lau |
| 7,201,169 B2 | 4/2007 | Wilkie et al. |
| 7,207,333 B2 | 4/2007 | Tohara |
| 7,210,481 B1 | 5/2007 | Lovell et al. |
| 7,219,669 B1 | 5/2007 | Lovell et al. |
| 7,225,811 B2 | 6/2007 | Ruiz et al. |
| 7,255,106 B2 | 8/2007 | Gallem et al. |
| 7,261,104 B2 | 8/2007 | Keifer |
| 7,287,528 B2 | 10/2007 | Ho et al. |
| 7,290,546 B2 | 11/2007 | Sprinkle et al. |
| 7,296,575 B1 | 11/2007 | Radney |
| 7,318,437 B2 | 1/2008 | Gunaratnam et al. |
| 7,353,827 B2 | 4/2008 | Geist |
| 7,357,136 B2 | 4/2008 | Ho et al. |

(56) References Cited

U.S. PATENT DOCUMENTS

| | | |
|---|---|---|
| 7,406,966 B2 | 8/2008 | Wondka et al. |
| 7,448,386 B2 | 11/2008 | Ho et al. |
| 7,487,772 B2 | 2/2009 | Ging et al. |
| 7,493,902 B2 | 2/2009 | White et al. |
| D589,139 S | 3/2009 | Guney |
| 7,523,754 B2 | 4/2009 | Lithgow et al. |
| 7,549,420 B2 | 6/2009 | Martinez et al. |
| D595,841 S | 7/2009 | McAuley et al. |
| 7,562,658 B2 | 7/2009 | Madaus et al. |
| 7,597,100 B2 | 10/2009 | Ging |
| 7,640,934 B2 | 1/2010 | Zollinger et al. |
| 7,647,926 B2 | 1/2010 | Gerder et al. |
| 7,658,189 B2 | 2/2010 | Davidson et al. |
| 7,665,464 B2 | 2/2010 | Kopacko et al. |
| D612,933 S | 3/2010 | Prentice |
| 7,681,575 B2 | 3/2010 | Wixey et al. |
| 7,694,677 B2 | 4/2010 | Tang |
| 7,703,457 B2 | 4/2010 | Barnett et al. |
| 7,708,017 B2 | 5/2010 | Davidson |
| 7,753,051 B2 | 7/2010 | Burrow et al. |
| D623,288 S | 9/2010 | Lubke |
| 7,814,911 B2 | 10/2010 | Bordewick et al. |
| 7,827,990 B1 | 11/2010 | Melidis et al. |
| 7,828,990 B1 | 11/2010 | Melidis |
| 7,856,982 B2 | 12/2010 | Matula et al. |
| 7,861,715 B2 | 1/2011 | Jones et al. |
| 7,877,817 B1 | 2/2011 | Ho |
| 7,896,003 B2 | 3/2011 | Matula et al. |
| 7,931,024 B2 | 4/2011 | Ho et al. |
| 7,934,501 B2 | 5/2011 | Fu |
| 7,942,150 B2 | 5/2011 | Guney et al. |
| 7,992,560 B2 | 8/2011 | Burton et al. |
| 8,042,539 B2 | 10/2011 | Chandran et al. |
| 8,042,541 B2 | 10/2011 | Amarasinghe et al. |
| 8,109,271 B2 | 2/2012 | Vandine et al. |
| 8,136,524 B2 | 3/2012 | Ging et al. |
| 8,136,525 B2 | 3/2012 | Lubke et al. |
| 8,171,933 B2 | 5/2012 | Xue et al. |
| D661,796 S | 6/2012 | Andrews et al. |
| 8,245,711 B2 | 8/2012 | Matula et al. |
| 8,272,382 B2 | 9/2012 | Howard et al. |
| 8,371,302 B2 | 2/2013 | Ging et al. |
| 8,397,727 B2 | 3/2013 | Ng et al. |
| 8,443,807 B2 | 5/2013 | McAuley et al. |
| D686,313 S | 7/2013 | Matula et al. |
| 8,479,726 B2 | 7/2013 | McAuley |
| 8,479,741 B2 | 7/2013 | McAuley et al. |
| 8,567,404 B2 | 10/2013 | Davidson et al. |
| 8,631,793 B2 | 1/2014 | Omura et al. |
| 8,631,799 B2 | 1/2014 | Davenport |
| 8,636,005 B2 | 1/2014 | Gradon et al. |
| 8,701,667 B1 | 4/2014 | Ho et al. |
| 8,714,157 B2 | 5/2014 | McAuley et al. |
| 8,720,444 B2 | 5/2014 | Chang |
| 8,757,157 B2 | 6/2014 | Price et al. |
| 8,783,257 B2 | 7/2014 | McAuley et al. |
| 8,869,797 B2 | 10/2014 | Davidson et al. |
| 8,869,798 B2 | 10/2014 | Wells et al. |
| 8,875,709 B2 | 11/2014 | Davidson et al. |
| 8,944,061 B2 | 2/2015 | D'Souza et al. |
| 8,950,404 B2 | 2/2015 | Formica et al. |
| 8,960,196 B2 | 2/2015 | Henry |
| 8,969,196 B2 | 3/2015 | Park |
| 9,010,331 B2 | 4/2015 | Lang et al. |
| 9,027,556 B2 | 5/2015 | Ng et al. |
| 9,032,955 B2 | 5/2015 | Lubke et al. |
| 9,032,956 B2 | 5/2015 | Scheiner et al. |
| 9,072,852 B2 | 7/2015 | McAuley et al. |
| 9,095,673 B2 | 8/2015 | Barlow et al. |
| 9,119,929 B2 | 9/2015 | McAuley et al. |
| 9,119,931 B2 | 9/2015 | D'Souza et al. |
| 9,138,555 B2 | 9/2015 | McAuley et al. |
| 9,149,596 B2 | 10/2015 | Valcic et al. |
| 9,186,474 B1 | 11/2015 | Rollins |
| 9,242,062 B2 | 1/2016 | Melidis et al. |
| 9,292,799 B2 | 3/2016 | McAuley et al. |
| 9,295,799 B2 | 3/2016 | McAuley et al. |
| 9,302,065 B2 | 4/2016 | Smith et al. |
| 9,320,566 B1 | 4/2016 | Alston, Jr. |
| 9,320,866 B2 | 4/2016 | McAuley et al. |
| 9,333,315 B2 | 5/2016 | McAuley et al. |
| 9,339,622 B2 | 5/2016 | McAuley et al. |
| 9,339,624 B2 | 5/2016 | McAuley |
| 9,375,545 B2 | 6/2016 | Darkin et al. |
| 9,381,316 B2 | 7/2016 | Ng et al. |
| 9,439,405 B2 | 9/2016 | Brüggemann |
| 9,457,162 B2 | 10/2016 | Ging et al. |
| 9,486,601 B2 | 11/2016 | Stallard et al. |
| 9,517,317 B2 | 12/2016 | McAuley et al. |
| 9,522,246 B2 | 12/2016 | Frater et al. |
| 9,539,405 B2 | 1/2017 | McAuley et al. |
| 9,550,038 B2 | 1/2017 | McAuley et al. |
| 9,561,338 B2 * | 2/2017 | McAuley .......... A61M 16/0633 |
| 9,561,339 B2 | 2/2017 | McAuley et al. |
| 9,744,385 B2 | 8/2017 | Henry et al. |
| 9,884,160 B2 | 2/2018 | McAuley et al. |
| 9,901,699 B2 | 2/2018 | Veliss et al. |
| 9,901,700 B2 | 2/2018 | McAuley et al. |
| 9,907,925 B2 | 3/2018 | McAuley et al. |
| 9,974,914 B2 | 5/2018 | McAuley |
| 10,080,856 B2 | 9/2018 | McLaren et al. |
| 10,137,271 B2 | 11/2018 | McAuley et al. |
| 10,201,678 B2 | 2/2019 | Guney et al. |
| 10,252,015 B2 | 4/2019 | McAuley et al. |
| 10,258,756 B2 | 4/2019 | Mainusch et al. |
| 10,258,757 B2 | 4/2019 | Allan et al. |
| 10,272,218 B2 | 4/2019 | McAuley et al. |
| 10,328,226 B2 | 6/2019 | Allan et al. |
| 10,363,387 B2 | 7/2019 | Allan et al. |
| 10,384,029 B2 | 8/2019 | McAuley et al. |
| 10,413,694 B2 | 9/2019 | Allan et al. |
| 10,463,825 B2 | 11/2019 | McAuley et al. |
| 10,742,451 B2 | 8/2020 | Tajalli |
| 10,792,451 B2 | 10/2020 | Allan et al. |
| 10,821,251 B2 | 11/2020 | McAuley et al. |
| 10,835,702 B2 | 11/2020 | McAuley et al. |
| 10,842,964 B2 | 11/2020 | McAuley et al. |
| 10,980,962 B2 | 4/2021 | McAuley et al. |
| 11,179,535 B2 | 11/2021 | McAuley et al. |
| 11,247,013 B2 | 2/2022 | McAuley et al. |
| 11,260,194 B2 | 3/2022 | McAuley et al. |
| 11,291,790 B2 | 4/2022 | McAuley et al. |
| 11,357,944 B2 | 6/2022 | McAuley et al. |
| 11,395,894 B2 | 7/2022 | McAuley et al. |
| 11,471,635 B2 | 10/2022 | McAuley et al. |
| 11,541,197 B2 | 1/2023 | McAuley et al. |
| 11,554,234 B2 | 1/2023 | McAuley et al. |
| 11,559,650 B2 * | 1/2023 | McAuley .......... A61M 16/0633 |
| 11,660,413 B2 | 5/2023 | McAuley et al. |
| 11,712,532 B2 | 8/2023 | McAuley et al. |
| 11,766,535 B2 | 9/2023 | McAuley et al. |
| 2001/0017134 A1 | 8/2001 | Bahr |
| 2001/0020474 A1 | 9/2001 | Hecker et al. |
| 2001/0029952 A1 | 10/2001 | Curran |
| 2002/0005198 A1 | 1/2002 | Kwok et al. |
| 2002/0014241 A1 | 2/2002 | Gradon et al. |
| 2002/0020416 A1 | 2/2002 | Namey |
| 2002/0026934 A1 | 3/2002 | Lithgow et al. |
| 2002/0029780 A1 | 3/2002 | Frater et al. |
| 2002/0039867 A1 | 4/2002 | Curro et al. |
| 2002/0046755 A1 | 4/2002 | Voss |
| 2002/0053347 A1 | 5/2002 | Ziaee |
| 2002/0059935 A1 | 5/2002 | Wood |
| 2002/0069467 A1 | 6/2002 | Immediato et al. |
| 2002/0092527 A1 | 7/2002 | Wood |
| 2002/0096173 A1 | 7/2002 | Berthon-Jones |
| 2002/0096176 A1 | 7/2002 | Gunaratnam et al. |
| 2002/0096178 A1 | 7/2002 | Ziaee |
| 2002/0100474 A1 | 8/2002 | Kellner et al. |
| 2002/0100479 A1 | 8/2002 | Scarberry et al. |
| 2002/0108613 A1 | 8/2002 | Gunaratnam et al. |
| 2002/0117177 A1 | 8/2002 | Kwok |
| 2003/0000533 A1 | 1/2003 | Olsen et al. |
| 2003/0005509 A1 | 1/2003 | Kelzer |

(56) References Cited

U.S. PATENT DOCUMENTS

| | | |
|---|---|---|
| 2003/0005931 A1 | 1/2003 | Jaffre et al. |
| 2003/0005933 A1 | 1/2003 | Izuchukwu |
| 2003/0019495 A1 | 1/2003 | Palkon et al. |
| 2003/0019496 A1 | 1/2003 | Kopacko et al. |
| 2003/0029454 A1 | 2/2003 | Gelinas et al. |
| 2003/0047185 A1 | 3/2003 | Olsen et al. |
| 2003/0051732 A1 | 3/2003 | Smith et al. |
| 2003/0075180 A1 | 4/2003 | Raje |
| 2003/0075182 A1 | 4/2003 | Heidmann et al. |
| 2003/0079749 A1 | 5/2003 | Strickland et al. |
| 2003/0084996 A1 | 5/2003 | Alberg et al. |
| 2003/0089373 A1 | 5/2003 | Gradon et al. |
| 2003/0094177 A1 | 5/2003 | Smith et al. |
| 2003/0121519 A1 | 7/2003 | Estes et al. |
| 2003/0145857 A1 | 8/2003 | Sullivan et al. |
| 2003/0149384 A1 | 8/2003 | Davis et al. |
| 2003/0164170 A1 | 9/2003 | Drew et al. |
| 2003/0172936 A1 | 9/2003 | Wilkie et al. |
| 2003/0196655 A1 | 10/2003 | Ging et al. |
| 2003/0196656 A1 | 10/2003 | Moore |
| 2003/0196658 A1 | 10/2003 | Ging et al. |
| 2003/0196659 A1 | 10/2003 | Gradon et al. |
| 2003/0196664 A1 | 10/2003 | Jacobson |
| 2003/0200970 A1 | 10/2003 | Stenzler et al. |
| 2003/0217746 A1 | 11/2003 | Gradon et al. |
| 2003/0221691 A1 | 12/2003 | Biener |
| 2004/0011087 A1 | 1/2004 | Rebouillat et al. |
| 2004/0025882 A1 | 2/2004 | Madaus et al. |
| 2004/0035427 A1 | 2/2004 | Bordewick et al. |
| 2004/0065328 A1 | 4/2004 | Amarasinghe et al. |
| 2004/0067333 A1 | 4/2004 | Amarasinghe |
| 2004/0092999 A1 | 5/2004 | Lojewski |
| 2004/0094157 A1 | 5/2004 | Dantanarayana et al. |
| 2004/0107968 A1 | 6/2004 | Griffiths |
| 2004/0112377 A1 | 6/2004 | Amarasinghe et al. |
| 2004/0112384 A1 | 6/2004 | Lithgow et al. |
| 2004/0112385 A1 | 6/2004 | Drew |
| 2004/0118212 A1 | 6/2004 | Orr et al. |
| 2004/0118406 A1 | 6/2004 | Lithgow |
| 2004/0118412 A1 | 6/2004 | Piletti-Reyes |
| 2004/0133604 A1 | 7/2004 | Ging |
| 2004/0139973 A1 | 7/2004 | Wright |
| 2004/0149280 A1 | 8/2004 | Semeniuk |
| 2004/0182398 A1 | 9/2004 | Sprinkle et al. |
| 2004/0211427 A1 | 10/2004 | Jones et al. |
| 2004/0221850 A1 | 11/2004 | Ging et al. |
| 2004/0226566 A1 | 11/2004 | Gunaratnam et al. |
| 2004/0255949 A1 | 12/2004 | Lang et al. |
| 2004/0261797 A1 | 12/2004 | White et al. |
| 2005/0011521 A1 | 1/2005 | Sprinkle et al. |
| 2005/0011524 A1 | 1/2005 | Thomlinson et al. |
| 2005/0016532 A1 | 1/2005 | Farrell |
| 2005/0016544 A1 | 1/2005 | Thornton |
| 2005/0028822 A1 | 2/2005 | Sleeper et al. |
| 2005/0028833 A1 | 2/2005 | Vena et al. |
| 2005/0033247 A1 | 2/2005 | Thompson |
| 2005/0045182 A1 | 3/2005 | Wood et al. |
| 2005/0051171 A1 | 3/2005 | Booth |
| 2005/0051177 A1 | 3/2005 | Wood |
| 2005/0066976 A1 | 3/2005 | Wondka |
| 2005/0076913 A1 | 4/2005 | Ho et al. |
| 2005/0092327 A1 | 5/2005 | Fini et al. |
| 2005/0098183 A1 | 5/2005 | Nash et al. |
| 2005/0121030 A1 | 6/2005 | Bateman et al. |
| 2005/0121037 A1 | 6/2005 | Wood |
| 2005/0133038 A1 | 6/2005 | Rutter |
| 2005/0150497 A1 | 7/2005 | Eifler et al. |
| 2005/0155604 A1 | 7/2005 | Ging et al. |
| 2005/0172969 A1 | 8/2005 | Ging |
| 2005/0199239 A1 | 9/2005 | Lang et al. |
| 2005/0199241 A1 | 9/2005 | Ging et al. |
| 2005/0199242 A1 | 9/2005 | Matula et al. |
| 2005/0205096 A1 | 9/2005 | Matula |
| 2005/0235999 A1 | 10/2005 | Wood et al. |
| 2005/0241644 A1 | 11/2005 | Guney et al. |
| 2006/0027237 A1 | 2/2006 | Sleeper |
| 2006/0032504 A1 | 2/2006 | Burton et al. |
| 2006/0042629 A1 | 3/2006 | Geist |
| 2006/0042632 A1 | 3/2006 | Bishop et al. |
| 2006/0054169 A1 | 3/2006 | Han et al. |
| 2006/0060200 A1 | 3/2006 | Ho et al. |
| 2006/0076019 A1 | 4/2006 | Ho |
| 2006/0081250 A1 | 4/2006 | Bordewick et al. |
| 2006/0081256 A1 | 4/2006 | Palmer |
| 2006/0096598 A1 | 5/2006 | Ho et al. |
| 2006/0102185 A1 | 5/2006 | Drew et al. |
| 2006/0107958 A1 | 5/2006 | Sleeper |
| 2006/0118117 A1 | 6/2006 | Berthon-Jones et al. |
| 2006/0124131 A1 | 6/2006 | Chandran |
| 2006/0130844 A1 | 6/2006 | Ho et al. |
| 2006/0137690 A1 | 6/2006 | Gunaratnam et al. |
| 2006/0169286 A1 | 8/2006 | Eifler et al. |
| 2006/0174887 A1 | 8/2006 | Chandran et al. |
| 2006/0178645 A1 | 8/2006 | Peppel |
| 2006/0196511 A1 | 9/2006 | Lau et al. |
| 2006/0201514 A1 | 9/2006 | Jones et al. |
| 2006/0207599 A1 | 9/2006 | Busch |
| 2006/0213516 A1 | 9/2006 | Hoffman |
| 2006/0225740 A1 | 10/2006 | Eaton et al. |
| 2006/0231103 A1 | 10/2006 | Matula et al. |
| 2006/0237017 A1 | 10/2006 | Davidson et al. |
| 2006/0237018 A1 | 10/2006 | McAuley et al. |
| 2006/0249159 A1 | 11/2006 | Ho |
| 2006/0254593 A1 | 11/2006 | Chang |
| 2006/0266361 A1 | 11/2006 | Hernandez |
| 2006/0283456 A1 | 12/2006 | Geiselhart et al. |
| 2006/0283458 A1 | 12/2006 | Woodard |
| 2006/0283459 A1 | 12/2006 | Geiselhart et al. |
| 2006/0283461 A1 | 12/2006 | Lubke et al. |
| 2007/0000492 A1 | 1/2007 | Hansel et al. |
| 2007/0010786 A1 | 1/2007 | Casey et al. |
| 2007/0044804 A1 | 3/2007 | Matula et al. |
| 2007/0062536 A1 | 3/2007 | McAuley |
| 2007/0089749 A1 | 4/2007 | Ho et al. |
| 2007/0107733 A1 | 5/2007 | Ho |
| 2007/0125384 A1 | 6/2007 | Zollinger et al. |
| 2007/0125385 A1 | 6/2007 | Ho et al. |
| 2007/0125387 A1 | 6/2007 | Zollinger et al. |
| 2007/0137653 A1 | 6/2007 | Wood |
| 2007/0142785 A1 | 6/2007 | Lundgaard et al. |
| 2007/0157353 A1 | 7/2007 | Guney et al. |
| 2007/0163594 A1 | 7/2007 | Ho et al. |
| 2007/0163600 A1 | 7/2007 | Hoffman |
| 2007/0174952 A1 | 8/2007 | Jacob |
| 2007/0175480 A1 | 8/2007 | Gradon et al. |
| 2007/0209663 A1 | 9/2007 | Marque et al. |
| 2007/0215158 A1 | 9/2007 | Kroupa et al. |
| 2007/0215161 A1 | 9/2007 | Frater et al. |
| 2007/0221227 A1 | 9/2007 | Ho |
| 2007/0227541 A1 | 10/2007 | Van Den |
| 2007/0267022 A1 | 11/2007 | Chiam |
| 2007/0272247 A1 | 11/2007 | Porat |
| 2007/0272249 A1 | 11/2007 | Chandran |
| 2007/0295335 A1 | 12/2007 | Nashed |
| 2008/0035152 A1 | 2/2008 | Ho et al. |
| 2008/0041388 A1 | 2/2008 | McAuley et al. |
| 2008/0041393 A1 | 2/2008 | Bracken |
| 2008/0047560 A1 | 2/2008 | Veliss et al. |
| 2008/0053446 A1 | 3/2008 | Sleeper et al. |
| 2008/0053450 A1 | 3/2008 | Van Kerkwyk et al. |
| 2008/0060648 A1 | 3/2008 | Thornton et al. |
| 2008/0060653 A1 | 3/2008 | Hallett et al. |
| 2008/0060657 A1 | 3/2008 | McAuley et al. |
| 2008/0066745 A1 | 3/2008 | Janbakhsh |
| 2008/0066755 A1 | 3/2008 | Janbakhsh |
| 2008/0078387 A1 | 4/2008 | Vandine |
| 2008/0078396 A1 | 4/2008 | Janbakhsh |
| 2008/0083412 A1 | 4/2008 | Henry et al. |
| 2008/0092905 A1 | 4/2008 | Gunaratnam |
| 2008/0099024 A1 | 5/2008 | Gunaratnam et al. |
| 2008/0105257 A1 | 5/2008 | Klasek et al. |
| 2008/0110464 A1 | 5/2008 | Davidson et al. |
| 2008/0127978 A1 | 6/2008 | Rubin et al. |
| 2008/0135050 A1 | 6/2008 | Hitchcock et al. |

(56) References Cited

U.S. PATENT DOCUMENTS

| | | |
|---|---|---|
| 2008/0142019 A1 | 6/2008 | Lewis |
| 2008/0149104 A1 | 6/2008 | Eifler |
| 2008/0171737 A1 | 7/2008 | Fensome |
| 2008/0178875 A1 | 7/2008 | Henry |
| 2008/0178886 A1 | 7/2008 | Lieberman et al. |
| 2008/0190432 A1 | 8/2008 | Blochlinger et al. |
| 2008/0190436 A1 | 8/2008 | Jaffe et al. |
| 2008/0196728 A1 | 8/2008 | Ho |
| 2008/0210241 A1 | 9/2008 | Schulz et al. |
| 2008/0223370 A1 | 9/2008 | Kim |
| 2008/0230068 A1 | 9/2008 | Rudolph |
| 2008/0236586 A1 | 10/2008 | Mcdonald et al. |
| 2008/0245369 A1 | 10/2008 | Matula et al. |
| 2008/0257354 A1 | 10/2008 | Davidson |
| 2008/0264422 A1 | 10/2008 | Fishman |
| 2008/0271739 A1 | 11/2008 | Facer et al. |
| 2008/0276937 A1 | 11/2008 | Davidson et al. |
| 2008/0302366 A1 | 12/2008 | McGinnis et al. |
| 2008/0314388 A1 | 12/2008 | Brambilla et al. |
| 2008/0314390 A1 | 12/2008 | Kwok et al. |
| 2008/0319334 A1 | 12/2008 | Yamamori |
| 2009/0014007 A1 | 1/2009 | Brambilla et al. |
| 2009/0032024 A1 | 2/2009 | Burz et al. |
| 2009/0044808 A1 | 2/2009 | Guney et al. |
| 2009/0078267 A1 | 3/2009 | Burz et al. |
| 2009/0090364 A1 | 4/2009 | Daugaard et al. |
| 2009/0107504 A1 | 4/2009 | McAuley et al. |
| 2009/0114227 A1 | 5/2009 | Gunaratnam et al. |
| 2009/0120442 A1 | 5/2009 | Ho |
| 2009/0126739 A1 | 5/2009 | Ng et al. |
| 2009/0133697 A1 | 5/2009 | Kwok et al. |
| 2009/0139527 A1 | 6/2009 | Ng et al. |
| 2009/0145429 A1 | 6/2009 | Ging et al. |
| 2009/0151729 A1 | 6/2009 | Judson et al. |
| 2009/0173349 A1 | 7/2009 | Hernandez et al. |
| 2009/0183734 A1 | 7/2009 | Kwok et al. |
| 2009/0183739 A1 | 7/2009 | Wondka |
| 2009/0188507 A1 | 7/2009 | Lacava |
| 2009/0211583 A1 | 8/2009 | Carroll et al. |
| 2009/0223519 A1 | 9/2009 | Eifler et al. |
| 2009/0223521 A1 | 9/2009 | Howard |
| 2009/0320842 A1 | 12/2009 | Doherty |
| 2009/0320851 A1 | 12/2009 | Selvarajan et al. |
| 2010/0000538 A1 | 1/2010 | Edwards et al. |
| 2010/0000539 A1 | 1/2010 | Woodard |
| 2010/0000543 A1 | 1/2010 | Berthon-Jones et al. |
| 2010/0006101 A1* | 1/2010 | McAuley .......... A61M 16/0633 128/206.24 |
| 2010/0037897 A1 | 2/2010 | Wood |
| 2010/0051031 A1 | 3/2010 | Lustenberger et al. |
| 2010/0051034 A1 | 3/2010 | Howard |
| 2010/0083969 A1 | 4/2010 | Crumblin |
| 2010/0108072 A1 | 5/2010 | D'Souza |
| 2010/0132717 A1 | 6/2010 | Davidson et al. |
| 2010/0154798 A1 | 6/2010 | Henry et al. |
| 2010/0170516 A1 | 7/2010 | Grane |
| 2010/0199992 A1 | 8/2010 | Ho |
| 2010/0229868 A1 | 9/2010 | Rummery et al. |
| 2010/0229872 A1 | 9/2010 | Ho |
| 2010/0258132 A1 | 10/2010 | Moore |
| 2010/0258136 A1 | 10/2010 | Doherty et al. |
| 2010/0294281 A1 | 11/2010 | Ho |
| 2010/0307502 A1 | 12/2010 | Rummery et al. |
| 2010/0313891 A1 | 12/2010 | Veliss et al. |
| 2010/0319700 A1 | 12/2010 | Ng et al. |
| 2010/0326445 A1 | 12/2010 | Veliss et al. |
| 2011/0067704 A1 | 3/2011 | Kooij |
| 2011/0072553 A1 | 3/2011 | Ho |
| 2011/0088699 A1* | 4/2011 | Skipper .............. A61M 16/06 128/206.26 |
| 2011/0126838 A1 | 6/2011 | Alberici |
| 2011/0146675 A1 | 6/2011 | Chen |
| 2011/0162654 A1 | 7/2011 | Carroll et al. |
| 2011/0232649 A1 | 9/2011 | Collazo et al. |
| 2011/0253156 A1 | 10/2011 | Sweeney |
| 2011/0259337 A1 | 10/2011 | Hitchcock et al. |
| 2011/0265796 A1 | 11/2011 | Amarasinghe et al. |
| 2011/0290253 A1 | 12/2011 | McAuley |
| 2012/0125339 A1 | 5/2012 | Ho et al. |
| 2012/0132208 A1 | 5/2012 | Judson et al. |
| 2012/0132209 A1 | 5/2012 | Rummery |
| 2012/0138061 A1 | 6/2012 | Dravitzki et al. |
| 2012/0204879 A1 | 8/2012 | Cariola et al. |
| 2012/0285457 A1 | 11/2012 | Mansour et al. |
| 2012/0304999 A1 | 12/2012 | Swift et al. |
| 2012/0318265 A1 | 12/2012 | Amirav et al. |
| 2013/0133659 A1 | 5/2013 | Ng et al. |
| 2013/0133664 A1 | 5/2013 | Startare |
| 2013/0152918 A1 | 6/2013 | Rummery et al. |
| 2013/0160769 A1 | 6/2013 | Ng et al. |
| 2014/0026888 A1 | 1/2014 | Matula |
| 2014/0083428 A1 | 3/2014 | Rothermel et al. |
| 2014/0083430 A1 | 3/2014 | Matula, Jr. et al. |
| 2014/0137870 A1 | 5/2014 | Barlow et al. |
| 2014/0261432 A1 | 9/2014 | Eves et al. |
| 2014/0290669 A1 | 10/2014 | Ngo |
| 2014/0311492 A1 | 10/2014 | Stuebiger et al. |
| 2014/0338672 A1 | 11/2014 | D'Souza et al. |
| 2014/0373834 A1 | 12/2014 | Gunaratnam et al. |
| 2015/0033457 A1 | 2/2015 | Tryner et al. |
| 2015/0090266 A1 | 4/2015 | Melidis et al. |
| 2015/0246198 A1 | 9/2015 | Bearne et al. |
| 2015/0335846 A1 | 11/2015 | Romagnoli et al. |
| 2015/0352308 A1 | 12/2015 | Cullen et al. |
| 2015/0374944 A1 | 12/2015 | Edwards et al. |
| 2016/0001028 A1 | 1/2016 | McAuley et al. |
| 2016/0008558 A1 | 1/2016 | Huddart et al. |
| 2016/0015922 A1 | 1/2016 | Chodkowski et al. |
| 2016/0038707 A1 | 2/2016 | Allan et al. |
| 2016/0051786 A1 | 2/2016 | McAuley et al. |
| 2016/0213873 A1 | 7/2016 | McAuley et al. |
| 2016/0213874 A1 | 7/2016 | Davidson et al. |
| 2016/0296720 A1 | 10/2016 | Henry et al. |
| 2017/0246411 A1 | 8/2017 | Mashal et al. |
| 2017/0296770 A1 | 10/2017 | Gunaratnam et al. |
| 2017/0368288 A1 | 12/2017 | Stephens et al. |
| 2018/0221615 A1 | 8/2018 | Sevincli |
| 2018/0250483 A1 | 9/2018 | Olsen et al. |
| 2018/0256844 A1 | 9/2018 | Galgali et al. |
| 2019/0001095 A1 | 1/2019 | Rose et al. |
| 2020/0046928 A1 | 2/2020 | Allan et al. |
| 2020/0171260 A1 | 6/2020 | McLaren |
| 2020/0197644 A1 | 6/2020 | McAuley et al. |
| 2021/0228829 A1 | 7/2021 | McAuley et al. |
| 2022/0105294 A1 | 4/2022 | McAuley et al. |
| 2022/0249794 A1 | 8/2022 | McAuley et al. |
| 2022/0331539 A1 | 10/2022 | McAuley et al. |
| 2023/0084024 A1 | 3/2023 | McAuley et al. |
| 2023/0086085 A1 | 3/2023 | McAuley et al. |
| 2023/0256188 A1 | 8/2023 | McAuley et al. |
| 2023/0381440 A1 | 11/2023 | Allan et al. |

FOREIGN PATENT DOCUMENTS

| | | |
|---|---|---|
| CA | 2648690 | 11/2007 |
| CD | 000966064-0001 | 9/2008 |
| CD | 000966064-0002 | 9/2008 |
| CD | 000966064-0003 | 9/2008 |
| CD | 000966064-0004 | 9/2008 |
| CD | 000966064-0017 | 9/2008 |
| CN | 2172538 | 7/1994 |
| CN | 1780265 | 12/2005 |
| CN | 1750854 | 3/2006 |
| CN | 1784250 | 6/2006 |
| CN | 1901961 | 1/2007 |
| CN | 101991897 A | 3/2011 |
| DE | 895692 | 11/1953 |
| DE | 29723101 U1 | 7/1998 |
| DE | 19603949 | 11/1998 |
| DE | 102005041717 | 4/2006 |
| DE | 102006011151 | 9/2007 |
| EP | 0 281 275 | 9/1988 |
| EP | 0 350 322 | 1/1990 |
| EP | 0 427 474 | 5/1991 |

(56) References Cited

FOREIGN PATENT DOCUMENTS

| | | |
|---|---|---|
| EP | 0 462 701 | 12/1991 |
| EP | 0 747 078 | 12/1996 |
| EP | 1 099 452 | 5/2001 |
| EP | 0 830 180 | 3/2002 |
| EP | 1 258 266 | 11/2002 |
| EP | 1 306 098 | 5/2003 |
| EP | 1 488 820 | 12/2004 |
| EP | 1 582 231 | 10/2005 |
| EP | 2 042 209 | 4/2009 |
| EP | 2 130 563 | 12/2009 |
| EP | 2 145 645 | 1/2010 |
| EP | 1 753 495 | 9/2010 |
| EP | 1 481 702 | 9/2012 |
| EP | 2 749 176 | 7/2014 |
| EP | 1 646 910 | 8/2015 |
| EP | 2 022 528 | 3/2016 |
| EP | 1 841 482 | 7/2016 |
| EP | 2 451 518 | 10/2017 |
| FR | 2658725 | 8/1991 |
| FR | 2749176 | 12/1997 |
| FR | 2823122 | 10/2002 |
| GB | 190224431 | 12/1902 |
| GB | 880824 | 10/1961 |
| GB | 979357 | 1/1965 |
| GB | 1467828 | 3/1977 |
| GB | 2133275 | 7/1984 |
| GB | 2173274 | 10/1986 |
| GB | 2186801 | 8/1987 |
| GB | 2385533 | 8/2003 |
| GB | 2408459 A | 1/2005 |
| GB | 2406797 A | 4/2005 |
| JP | 62-024721 | 2/1987 |
| JP | H09-010311 | 1/1997 |
| JP | 2000-325481 | 11/2000 |
| JP | 2004-016488 | 1/2004 |
| JP | 2005-529687 | 10/2005 |
| JP | 2005-537906 | 12/2005 |
| JP | 2007-516750 | 6/2007 |
| NZ | 531332 | 2/2004 |
| NZ | 534606 | 8/2004 |
| NZ | 528029 | 3/2005 |
| NZ | 548575 | 7/2006 |
| NZ | 551103 | 11/2006 |
| NZ | 567740 | 12/2009 |
| WO | WO 82/003548 | 10/1982 |
| WO | WO 97/00092 | 1/1997 |
| WO | WO 97/32494 | 9/1997 |
| WO | WO 97/45154 | 12/1997 |
| WO | WO 98/04310 | 2/1998 |
| WO | WO 98/04311 | 2/1998 |
| WO | WO 98/018514 | 5/1998 |
| WO | WO 98/024499 | 6/1998 |
| WO | WO 98/048878 | 11/1998 |
| WO | WO 98/57691 | 12/1998 |
| WO | WO 99/04842 | 2/1999 |
| WO | WO 99/43375 | 9/1999 |
| WO | WO 99/058181 | 11/1999 |
| WO | WO 99/058198 | 11/1999 |
| WO | WO 00/050122 | 8/2000 |
| WO | WO 00/057942 | 10/2000 |
| WO | WO 00/069497 | 11/2000 |
| WO | WO 00/74509 | 12/2000 |
| WO | WO 00/074758 | 12/2000 |
| WO | WO 00/078384 | 12/2000 |
| WO | WO 01/00266 | 1/2001 |
| WO | WO 01/32250 | 5/2001 |
| WO | WO 01/041854 | 6/2001 |
| WO | WO 01/058293 | 8/2001 |
| WO | WO 01/062326 | 8/2001 |
| WO | WO 01/89381 | 11/2001 |
| WO | WO 01/94721 | 12/2001 |
| WO | WO 01/097892 | 12/2001 |
| WO | WO 01/97892 | 12/2001 |
| WO | WO 01/097893 | 12/2001 |
| WO | WO 02/005883 | 1/2002 |
| WO | WO 02/011804 | 2/2002 |
| WO | WO 02/047749 | 6/2002 |
| WO | WO 02/074372 | 9/2002 |
| WO | WO 03/035156 | 5/2003 |
| WO | WO 03/076020 | 9/2003 |
| WO | WO 03/082406 | 10/2003 |
| WO | WO 03/092755 | 11/2003 |
| WO | WO 04/007010 | 1/2004 |
| WO | WO 04/096332 | 1/2004 |
| WO | WO 04/012803 | 2/2004 |
| WO | WO 04/022146 | 3/2004 |
| WO | WO 04/022147 | 3/2004 |
| WO | WO 04/030510 | 4/2004 |
| WO | WO 04/030736 | 4/2004 |
| WO | WO 04/041341 | 5/2004 |
| WO | WO 04/041342 | 5/2004 |
| WO | WO 04/052438 | 6/2004 |
| WO | WO 04/071565 | 8/2004 |
| WO | WO 04/073777 | 9/2004 |
| WO | WO 04/073778 | 9/2004 |
| WO | WO 04/079066 | 9/2004 |
| WO | WO 05/010608 | 2/2005 |
| WO | WO 05/016403 | 2/2005 |
| WO | WO 05/018523 | 3/2005 |
| WO | WO 05/021075 | 3/2005 |
| WO | WO 05/051468 | 6/2005 |
| WO | WO 05/063326 | 7/2005 |
| WO | WO 05/063328 | 7/2005 |
| WO | WO 05/076874 | 8/2005 |
| WO | WO 05/079726 | 9/2005 |
| WO | WO 05/086943 | 9/2005 |
| WO | WO 05/086946 | 9/2005 |
| WO | WO 05/097247 | 10/2005 |
| WO | WO 05/123166 | 12/2005 |
| WO | WO 06/000046 | 1/2006 |
| WO | WO 06/050559 | 5/2006 |
| WO | WO 06/069415 | 7/2006 |
| WO | WO 06/074513 | 7/2006 |
| WO | WO 06/074514 | 7/2006 |
| WO | WO 06/074515 | 7/2006 |
| WO | WO 06/096924 | 9/2006 |
| WO | WO 06/130903 | 12/2006 |
| WO | WO 06/138346 | 12/2006 |
| WO | WO 06/138416 | 12/2006 |
| WO | WO 07/006089 | 1/2007 |
| WO | WO 07/009182 | 1/2007 |
| WO | WO 07/021777 | 2/2007 |
| WO | WO 07/022562 | 3/2007 |
| WO | WO 07/041751 | 4/2007 |
| WO | WO 07/041786 | 4/2007 |
| WO | WO 07/045008 | 4/2007 |
| WO | WO 07/048174 | 5/2007 |
| WO | WO 07/053878 | 5/2007 |
| WO | WO 07/114492 | 10/2007 |
| WO | WO 07/147088 | 12/2007 |
| WO | WO 08/007985 | 1/2008 |
| WO | WO 08/011682 | 1/2008 |
| WO | WO 08/014543 | 2/2008 |
| WO | WO 08/030831 | 3/2008 |
| WO | WO 08/036625 | 3/2008 |
| WO | WO 08/043134 | 4/2008 |
| WO | WO 08/060295 | 5/2008 |
| WO | WO 08/068966 | 6/2008 |
| WO | WO 08/070929 | 6/2008 |
| WO | WO 08/106716 | 9/2008 |
| WO | WO 08/148086 | 12/2008 |
| WO | WO 09/026627 | 3/2009 |
| WO | WO 09/022248 | 4/2009 |
| WO | WO 09/052560 | 4/2009 |
| WO | WO 09/059353 | 5/2009 |
| WO | WO 09/092057 | 7/2009 |
| WO | WO 09/109005 | 9/2009 |
| WO | WO 09/133561 | 11/2009 |
| WO | WO 09/139647 | 11/2009 |
| WO | WO 10/066004 | 6/2010 |
| WO | WO 10/073142 | 7/2010 |
| WO | WO 10/131189 | 11/2010 |
| WO | WO 10/135785 | 12/2010 |
| WO | WO 10/148453 | 12/2010 |

(56) References Cited

FOREIGN PATENT DOCUMENTS

| | | |
|---|---|---|
| WO | WO 11/014931 | 2/2011 |
| WO | WO 11/059346 | 5/2011 |
| WO | WO 11/060479 | 5/2011 |
| WO | WO 11/077254 | 6/2011 |
| WO | WO 12/040791 | 4/2012 |
| WO | WO 12/045127 | 4/2012 |
| WO | WO 12/052902 | 4/2012 |
| WO | WO 12/143822 | 10/2012 |
| WO | WO 14/015382 | 1/2014 |
| WO | WO 14/020469 | 2/2014 |
| WO | WO 14/109749 | 7/2014 |
| WO | WO 14/175752 | 10/2014 |
| WO | WO 14/175753 | 10/2014 |
| WO | WO 15/033287 | 3/2015 |
| WO | WO 16/000040 | 1/2016 |
| WO | WO 17/049356 | 3/2017 |
| WO | WO 17/049357 | 3/2017 |
| WO | WO 18/007966 | 1/2018 |
| WO | WO 18/064712 | 4/2018 |

OTHER PUBLICATIONS

Applicant's Outline of Submissions in the matter of Australian Patent Application Nos. 2020223628, 2021201838, 2021201840, 2021201841, 2021201842, 2021201843 dated Mar. 20, 2024, 72 pp.
Australian Examination Report for Patent Application No. 2012265597 dated Dec. 19, 2013, in 5 pages.
Australian Examination Report in patent application No. 2010241390, dated Jan. 9, 2015, 4 pages.
Australian Examination Report in patent application No. 2015201920, dated Jul. 20, 2015, 3 pages.
Australian examination report in patent application No. 2016202801, dated Jun. 20, 2016, 2 pages.
Australian Examination Report in patent application No. 2010241390, dated Sep. 28, 2016, 4 pages.
Australian Examination Report in patent application No. 2010246985, dated Mar. 4, 2014, 5 pages.
Australian Examination Report in patent application No. 2015202814, dated Aug. 14, 2015, 8 pages.
Australian Examination Report in patent application No. 2016202799, dated May 31, 2016, 2 pages.
Australian Examination Report No. 1, in patent application No. AU 2013300237, dated Jun. 8, 2017, in 4 pages.
Australian Examination Report No. 2 for patent application No. 2018217307, dated Mar. 3, 2020, 4 pp.
Australian Examination Report; Application No. 2007273324; dated May 22, 2012; 4 pages.
Brazilian office action dated Jul. 11, 2019 in patent application No. BR11201211420-4.
Canadian Examination Report for Application No. 2655839 dated Oct. 4, 2013, in 2 pages.
Canadian Examination Report for patent application No. 2880749, dated Feb. 28, 2020, 4 pp.
Canadian Examination Report in patent application No. 2998247, dated Jan. 8, 2019, 4 pages.
Canadian Examination Report in patent application No. 2780310, dated Jul. 26, 2016, 4 pages.
Canadian Examination Report in patent application No. 2918167, dated Oct. 3, 2016, 4 pages.
Canadian Examination Report in patent application No. 2780310, dated Jan. 25, 2018 4 pages.
Canadian Examination Report in patent application No. 2780310, dated Oct. 9, 2018, 3 pp.
Canadian Examination Report in patent application No. 2880749, dated May 16, 2019, 5 pages.
Canadian Examination Report in patent application No. 2890556, dated Nov. 28, 2016, 4 pages.
Canadian Examination Report in patent application No. 3010066, dated Dec. 19, 2019, 4 pages.
Canadian Examination Report in patent application No. 3010066, dated May 3, 2019, 4 pages.
Canadian Examination Report in patent application No. 3017161, dated Apr. 22, 2020. 4 pp.
Canadian Examination Report in patent application No. 3017161, dated Aug. 21, 2019, 3 pp.
Chinese Examination Report in patent application No. 201080028029.0, dated Mar. 27, 2014, 16 pages.
Chinese Examination Report in patent application No. 2007800266164, dated Feb. 17, 2011, 18 pages.
Chinese Examination Report in patent application No. 201080061122.1, dated Jul. 17, 2015, 10 pages.
Chinese examination report in patent application No. 201210080441,8, dated Dec. 1, 2014, 1 pp. (English translation).
Chinese examination report in patent application No. 201210080441.8, dated Mar. 4, 2014, 11 pp. (English translation).
Chinese Examination Report in patent application No. 201610114706.X, dated Jul. 30, 2018, 9 pp., with translation.
Chinese Examination Report; dated Sep. 14, 2015; Application No. 201080028029.0; 3 pages.
Chinese Examination Report; dated Sep. 3, 2014; Application No. 201080061122.1; 7 pages.
Chinese First Office Action in patent application No. 201710824612.6, dated Sep. 30, 2019, 25 pp.
Chinese Fourth Office Action in patent application No. 201610116121.1, dated Sep. 30, 2019, 12 pages.
Chinese Office Action in patent application No. 201610116121.1, dated Sep. 28, 2017, 5 pages.
Chinese Second Examination Report in patent application No. 201610114706.X, dated Apr. 24, 2019 8 pp., with translation.
Chinese Second Office Action in patent application No. 201710824612.6, dated May 25, 2020. 19 pages.
Chinese Second Office Action; dated Jan. 19, 2015; Application No. 201080028029.0; 30 pages.
Chinese Third Examination Report in patent application No. 201610114706.X, dated Jan. 16, 2020, with translation. 32 pages.
Chinese Third Office Action in patent application No. 201810116121.1, dated Apr. 28, 2019, 16 pages.
Decision Denying Institute of Inter Partes Review dated Jul. 16, 2019 in IRP2019-00179, 32 pp.
Decision to Institute dated Jul. 16, 2019 in IPR2019-00180, 34 pp.
English Translation of JP Examination Report; dated Feb. 10, 2014; Application No. 2012-510418; 8 pages.
European examination report dated Jun. 16, 2020 in patent application No. 18163847.9, 5 pp.
European Examination Report dated Mar. 16, 2020 in patent application No. 18195537.8. 7 pages.
European examination report dated Sep. 5, 2019 in patent application No. 18163847.9, 5 pp.
European Examination Report in patent application No. 09746823.5, dated Apr. 3, 2017, 2 pages.
European Examination Report in patent application No. 07808683.2, dated May 9, 2018, 5 pages.
European Examination Report, European Application 13828380.9, dated Apr. 7, 2017, 8 pp.
U.S. Appl. No. 60/493,515, filed Aug. 8, 2002, Sleeper et al.
U.S. Appl. No. 60/496,059, filed Aug. 18, 2003, Ho et al.
U.S. Appl. No. 60/529,696, filed Dec. 16, 2003, Lithgow et al.
U.S. Appl. No. 61/064,406, filed Mar. 4, 2008, Wehbeh.
U.S. Appl. No. 61/071,893, filed May 22, 2008, Wehbeh et al.
U.S. Appl. No. 61/136,617, filed Sep. 19, 2008, Wehbeh et al.
Resmed Mirage Swift™ II Nasal Pillows System product page (http://www.resmed.com/en-us/products/masks/mirage_swift_II_nasal_pillows._system/Mirage-Swift-II-Nasal-Pillows-System.html?menu=products); archived Jul. 21, 2008, 2 pp.
Resmed Mirage Swift™ II user brochure (http://www.resmed.com/en us/products/masks/mirage-swift_II_nasal_pillows_system/documents/mirage-swift-ii-np-brochure-patient-english-usa.pdf) copyright 2007, 4 pp.
ResMed Mirage Swift II Fitting guide (http://www;resmed.com/en-us/products/masks/mirage_swift_II_nasal_pillows_system/documents/mirage-swift_ii_np-fitting_English.pdf) copyright 2006, 2 pp.

(56) References Cited

OTHER PUBLICATIONS

ResMed Mirage Swift II comparison to older Swift patient interface (http://www.resmed.com/en-us/products/masks/mirage_swift_II_nasal_pillows_system/documents/mirage-swift-ii-np-comparison-guide.pdf, 2007, 6 pp.
ResMed Mirage Swift II user guide (http://www.resmed.com/en-us/products/service_and_support/documents/60893rl_mirage_swiftII_nasal_userglide_us_multi.pdf) copyright 2006, 1 p.
ResMed Mirage Swift II component card (http://www.resmed.com/en-us/products/masks/mirage_swift_II_nasal_pillows_system/documents/mirage-swift-ii-np-cc-USA.pdf); copyright 2006, 2 pp.
Resmed Swift™ LT Nasal Pillows System, product page, (http://www.resmed.com/en-us/products/masks/mirage_swift_II_nasal_pillows_system/Mirage-Swift-II-Nasal_Pillows- System.html?menu=products), Jul. 3, 2008, 2 pp.
Resmed Swift LT user brochure, (http://www.resmed.com/en-us/products/masks/mirage_swift_II_nasal_pillows_system/documents/mirage-swift-ii-np-brochure-patient-english-usa.pdf), copyright 2008, 4 pp.
Resmed Swift™ LT component card (http://www.resmed.com/en-us/assets/documents/product/swift_It/components_card/1012463_swift-It_components-card_usa_eng.pdf) copyright 2008, 46 pp.
Resmed Swift™ LT fitting guide, (http://www.resmed.com/en-us/assets/documents/product/swift-II/clinical_fact_sheet/1012406 swift-ii_fact-sheet_usa_eng.pdf), 2008, 2 pp.
Resmed Swift™ LT fact sheet (http://www.resmcd.com/en-us/assets/documents/product/swift-It/clinical_fact_sheet/1012406 swiftIt_fact-sheet_usa_eng.pdf, copyright 2008, 4 pp.
Resmed Swift™ LT image gallery (http://www.resmed.com/en-us/products/masks/swift_It_nasal_pillows_system/imagegallery.html?menu=products, Apr. 25, 2008, 2 pp.
Resmed Swift™ LT interactive fitting guide—screenshot from troubleshooting part (http://www.resmed.com/enus/assets/multimedia/product/swift-It/flash/swift-It-fitting-eng.swf), Jul. 3, 2008, 2 pp.
Puritan Bennett Breeze® SleepGear® CPAP Interface, product page (http://puritanbennett.com/prod/product.aspx?id=233); archived Oct. 19, 2007, 2 pp.
Bennett Breeze® SleepGear® User's Guide (http://puritanbennett.com/_catalog/pdf/dfu/107598a00[I].pdf); copyright 2007, 18 pp.
Bennett Breeze® SleepGear® sales sheet (http://www.puritanbennett.com/_Catalog/PDF/Product/BreezeSleepGear.pdf) copyright 2016, 7 PP.
Bennett mask coding matrix (http://www.puritanbennett.com/_Catalog/PDF/Product/BreezeSlpGear(ST03700).pdf) copyright 2006, 3 pp.
Puritan Bennett Breeze fitting guide (http://www.puritanbennett.com/_Catalog/PDF/Product/BreezeFittingPoster.pdf, Oct. 19, 2007, 1 p.
Respironics Optilife Pillows mask product page (http://optilife.respironics.com:80/); archived Nov. 21, 2007, 2 pp.
Respironics Optilife Pillows mask part numbers page (http://optilife.respironics.com:80/Parts.aspx); archived Nov. 23, 2007, 4 pp.
Respironics Optilife Pillows mask FAQ (http://optilife.respironics.com:80/faqs.aspx); archived Nov. 23, 2007, 6 pp.
Respironics Optilife Pillows mask feature page (http://optilife.respironics.com:80/features.aspx); archived Nov. 23, 2007, 4 pp.
Respironics Optilife Pillows mask fitting guide screen shot (http://optilife.respironics.com:80/fittingGuide.aspx); archived Aug. 7, 2008, 1 p.
Respironics Optilife Pillows mask adjustment video screenshots, https://www.youtube.com/watch?v=shjcNmvvcBA); uploaded Aug. 3, 2008, 2 pp.
Puritan Bennett Breeze description; copyright 2000 by Mallinckrodt Inc., 4 pp.
Fisher & Paykel Opus product page, archived Sep. 3, 2009, 2 pp.
Fisher & Paykel Opus patient interface product photographs, Jul. 2007, 6 pp.
Photographs of Opus 360 nasal pillows mask patient instructions RevB, Jul. 2007, 4 pp.
Respironics Optilife brochure detailing updates; copyright 2008; dated Mar. 26, 2008, 3 pp.
Fisher & Paykel Opus product page, archived Sep. 7, 2009, 2 pp.
Fisher & Paykel Opus "Off-the-lips" pillows explanation page, archived Aug. 23, 2009, 2 pp.
Fisher & Paykel Opus "Off-the-lips" patient interface brochure, archived Oct. 14, 2009, 6 pp.
Fisher & Paykel Opus user-guide, archived Nov. 17, 2009, 2 pp.
Fisher & Paykel HC200 Series Nasal CPAP Blower & Heated Humidifier User Manual, 17 pp., May 1998.
Fisher & Paykel Healthcare, FlexiFit® 431 Full Face Mask instructions, 2010, 4 pp.
Fisher & Paykel Healthcare, FlexiFit™ 431 Full Face Mask, specification sheet, 2004, 2 pp.
Fisher & Paykel Healthcare, Interface Solutions Product Profile, 2006, 12 pp.
Fisher & Paykel MR810 Manual, Rev. C, 2004, 43 pp.
HomeDepot.com—Ring Nut Sales Page (Retrieved Oct. 16, 2015 from http://www.homedepot.com/p/Everbilt-1-2-in-Galvanized-HexNut-804076/20464- 7893), 4 pp.
Malloy, 1994, Plastic Part Design for Injection Molding, Hanser Gardner Publications, Inc, Cincinnati, OH, 14 pp.
Merriam-Webster's Collegiate Dictionary, Eleventh Edition, 2004, pp. 703, 905, 1074, 1184.
Philips Respironics 'System One Heated Humidifier—User Manual', 2011, pp. 1-16, [retrieved on Nov. 25, 2013] from the internet: URL: http://www.cpapxchange.com/cpap-machines-biap-machines/system-one-60-seri- es-cpap-humidifier-manual.pdf front cover, pp. 3-4 and 6.
ResMed FlexiFit brochure.
ResMed Exhibit, FlexiFit™ 431, product brochure, web pages (Wayback Machine), 2006, 23 pp.
ResMed Origins Brochure (Retrieved Apr. 17, 2016 from http://www.resmed.com/us/dam/documents/articles/resmedorigins.pdf), 64 pp.
ResMed Ultra Mirage™ Full Face Mask, product brochure, 2004, 2 pp.
ResMed Ultra Mirage™ Full Face Mask, product brochure, web pages (Wayback Machine), 2006, 9 pp.
ResMed, Jun. 29, 1997, Mask Frames (Source: Wayback Machine Internet Archive); http://web.archive.org/web/19970629053430/http://www.resmed.com- /maskframes/mask.htm, 2 pp/.
ResMed, Mirage Swift™ Nasal Pillows System from ResMed, product brochure, 2004, 6 pp.
ResMed, Mirage Swift™ Nasal Pillows System: User's Guide, product brochure, 2004, 11 pp.
ResMed, Mirage Vista™ Nasal Mask: Components Card, product brochure, 2005, 1 p.
The American Heritage Dictionary of the English Language, Fourth Edition, 2006, pp. 1501, 1502, 1650.
WeddingBands.com—Men's Wedding Ring Shopping Page (Retrieved Oct. 16, 2015 from http://www.weddingbands.com/ProductPop.sub.--wedding.sub.--band- s.sub.--metal/48214W.html), 3 pp.
ResMed, Oct. 1999, Mirage® Full Face Mask Update, Product Bulletin No. 161, 3 pp.
ResMed, Dec. 6, 1998, Mirage Full Face Cushion—Medium, drawing, 1 p.
ResMed, Jun. 20, 2000, Brochure, Mirage Full Face Mask, 5 pp.
ResMed, Oct. 4, 2000, Mirage® Full Face Mask, User's Guide, 3 pp.
U.S. Appl. No. 61/064,406, 34 pages, provided by USPTO on Feb. 23, 2009.
U.S. Appl. No. 61/071,893, 43 pages, provided by USPTO on Feb. 23, 2009.
U.S. Appl. No. 61/136,617, 82 pages, provided by USPTO on Feb. 23, 2009.
Petition for Inter Partes Review of U.S. Pat. No. 8,479,741 Pursuant to 35 U.S.C. §§ 311-19, 37 C.F.R. § 42, IPR2016-01714, dated Sep. 7, 2016.
Patent Owner Preliminary Response to Petition for Inter Partes Review of U.S. Pat. No. 8,479,741, IPR2016-01714, filed Dec. 14, 2016.

(56) References Cited

OTHER PUBLICATIONS

Decision Denying Institution of Inter Partes Review of U.S. Pat. No. 8,479,741 Pursuant to 37 C.F.R. § 42.108, IPR2016-01714, entered Mar. 10, 2017.
Declaration of Dr. John Izuchukwu, Ph.D., P.E., U.S. Pat. No. 8,443,807, IPR Nos. 2016-1726 & 2016-1734, dated Sep. 7, 2016.
Declaration of Dr. John Izuchukwu, Ph.D., P.E., U.S. Pat. No. 8,479,741, IPR Nos. 2016-1714 & 2016-1718, dated Sep. 7, 2016.
Patent Owner Preliminary Response to Petition for Inter Partes Review of U.S. Pat. No. 8,479,741, IPR2016-01718, filed Dec. 16, 2016.
Decision Denying Institution of Inter Partes Review of U.S. Pat. No. 8,479,741 Pursuant to 37 C.F.R. § 42.108, IPR2016-01718, entered Mar. 13, 2017.
Petition for Inter Partes Review of U.S. Pat. No. 8,479,741 Pursuant to 35 U.S.C. §§ 311-19, 37 C.F.R. § 42, IPR2016-01718, dated Sep. 7, 2016.
Petition for Inter Partes Review of U.S. Pat. No. 8,443,807 Pursuant to 35 U.S.C. §§ 311-19, 37 C.F.R. § 42, IPR2016-01726, dated Sep. 7, 2016.
Patent Owner Preliminary Response to Petition for Inter Partes Review of U.S. Pat. No. 8,443,807, IPR2016-01726, filed Dec. 13, 2016.
Decision Denying Institution of Inter Partes Review of U.S. Pat. No. 8,443,807 Pursuant to 37 C.F.R. § 42.108, IPR2016-01726, entered Mar. 6, 2017.
Petition for Inter Partes Review of U.S. Pat. No. 8,443,807 Pursuant to 35 U.S.C. §§ 311-19, 37 C.F.R. § 42, IPR2016-01734, dated Sep. 7, 2016.
Patent Owner Preliminary Response to Petition for Inter Partes Review of U.S. Pat. No. 8,443,807, IPR2016-01734, filed Dec. 22, 2016.
Decision Denying Institution of Inter Partes Review of U.S. Pat. No. 8,443,807 Pursuant to 37 C.F.R. § 42.108, IPR2016-01734, entered Mar. 13, 2017.
File History of U.S. Pat. No. 8,479,741 to McAuley et al, published Oct. 1, 2009.
File History of U.S. Pat. No. 8,443,807 to McAuley et al, published Jan. 7, 2010.
Patent Owner's Complaint for *Fisher & Paykel Healthcare Ltd.* v. *ResMed Corp.*, Case No. 2:16-cv- 06099-R-AJW (C.D. Cal.), dated Aug. 15, 2016.
Patent Owner's Notice of Voluntary Dismissal Without Prejudice for *Fisher & Paykel Healthcare Ltd.* v. *ResMed Corp.*, Case No. 2:16-cv-06099-R-AJW (C.D. Cal.), dated Aug. 16, 2016.
Patent Owner's Complaint for *Fisher & Paykel Healthcare Ltd.* v. *ResMed Corp.*, Case No. 3:16-cv-02068-GPC-WVG (S.D. Cal.), dated Aug. 16, 2016.
Petitioners' Complaint for *ResMed Inc., et al.* v. *Fisher & Paykel Healthcare Corp. Ltd., et al.*, Case No. 3:16-cv-02072-JAH-MDD (S.D. Cal.), dated Aug. 16, 2016.
Petitioners' Notice of Voluntary Dismissal Without Prejudice for *ResMed Inc., et al.* v. *Fisher & Paykel Healthcare Corp. Ltd., et al.*, Case No. 3:16-cv-02072-JAH-MDD (S.D. Cal.), dated Aug. 18, 2016.
Statutory Declaration made by Alistair Edwin McAuley, Apr. 9, 2015, in the matter of an Opposition by Fisher & Paykel Healthcare Limited of Australian patent application 2009221630 in the name of ResMed Limited.
Statutory Declaration made by Alistair Edwin McAuley, Apr. 14, 2015, in the matter of an Opposition by Fisher & Paykel Healthcare Limited of Australian patent application 2009221630 in the name of ResMed Limited.
Statutory Declaration made by Alistair Edwin McAuley, Apr. 17, 2015, in the matter of an Opposition by Fisher & Paykel Healthcare Limited of Australian patent application 2009221630 in the name of ResMed Limited.
Statutory Declaration made by Alistair Edwin McAuley, Sep. 16, 2015, in the matter of an Opposition by Fisher & Paykel Healthcare Limited of Australian patent application 2009221630 in the name of ResMed Limited.
First Affidavit of Alistair Edwin McAuley, Dec. 5, 2016, in the matter of *Fisher and Paykel Healthcare Limited* v. *ResMed Limited* filed in the Federal Court of Australia.
Second Affidavit of Alistair Edwin McAuley, Dec. 21, 2016, in the matter of *Fisher and Paykel Healthcare Limited* v. *ResMed Limited* filed in the Federal Court of Australia.
Third Affidavit of Alistair Edwin McAuley, Jan. 31, 2017, in the matter of *Fisher and Paykel Healthcare Limited* v. *ResMed Limited* filed in the Federal Court of Australia, 284 pp.
Declaration of Anthony Michael Ging in IPR 2019-000172, IPR 2019-000173, IPR 2019-000177, IPR 2019-000178, dated Nov. 8, 2018, 329 pp.
McGraw-Hill Dictionary of Scientific and Technical Terms, Sixth Edition, 2003, Tube, p. 2200.
Claim Chart for AirFit P10, U.S. Pat. No. 9,333,315, dated Nov. 7, 2018, 3 pp.
Affidavit of Martina Elise Muellers regarding the purchase of a sample of the "Respironics ComfortClassic nasal mask".
An extract of parallel infringement proceedings on the basis of the opposed patent that a reinforcing member necessarily limits the lateral expansion of the cushion, dated Sep. 16, 2016, 3 pp.
Cleaning Instruction for the "Respironics ComfortClassic nasal mask" dated 2002, 4 pp.
A submission of Jan. 2, 2018 in parallel proceedings in New Zealand.
Declaration of Greg Olsen regarding the "Respironics ComfortClassic nasal mask".
Excerpt from a notice of Sep. 6, 2017 in parallel proceedings pending in Germany.
Excerpt from a notice of Sep. 8, 2018 in parallel proceedings pending in Australia, 3 pp.
Excerpt from a submission of Jan. 31, 2017 in parallel proceedings pending in New Zealand, 2 pp.
Expert opinion of Mr. Herbert T. Bauer, dated Sep. 4, 2017, 18 pp.
Extract of patentee's submission of Oct. 24, 2016 made in preliminary injunction proceedings based on the opposed patent.
FDA Home Medical Devised Databases, 510(k) Premarket Notification, 3 pp., Decision Date Jan. 31, 1996.
Feature analysis of claim 1 of EP 1 841 482 B1.
ResMed, Instruction manual of the "MAP Papillon mask", 2005.
Instructions for Use for the "Respironics ComfortClassic Nasal Mask" (English and German version), 7 pp.
Invoice for a Respironics ComfortClassic nasal mask, dated Jun. 13, 2003.
Letter of May 16, 2018 from the procedure of European patent No. EP 1 841 482 B1 with enclosures.
Opposition Division preliminary opinion in EP 1 841 482 B1 (with enclosures), filed Aug. 22, 2019.
Overview table regarding the auxiliary requests filed by the patentee, submitted May 16, 2018, 1 p.
Respironics Inc, Securities and Exchange Commission Form 10-K Annual Report, Jun. 30, 1998, 79 pp.
Respironics Monarch Mini, 1 p. with 7 pp. of photos dated Jul. 20, 2005.
Respironics, Inc, Sep. 30, 1997, Solo™ CPAP System, User Instructions, 33 pp.
Respironics ComfortCurve, 1 p. with 7 pp. of photos dated Nov. 4, 2005.
Affidavit of Christopher Bryn Sparks regarding European patent No. EP1841482B1, dated Nov. 12, 2018, 5 pp.
Affidavit of Christopher Earl Nightingale regarding European patent No. EP1841482B1, dated May 15, 2018, 16 pp.
Affidavit of Christopher Earl Nightingale regarding European patent No. EP1841482B1, dated May 9, 2018, 22 pp.
Affidavit of Richard Joseph Lordo regarding European patent No. EP1841482B1, dated Nov. 26, 2019, 3 pp.
Affidavit of Richard Joseph Lordo regarding European patent No. EP1841482B1, dated Nov. 29, 2018, 5 pp.

(56) References Cited

OTHER PUBLICATIONS

Department of Health and Human Services, May 7, 1997, Premarket Notification [501(k)] review, Appendix 2, ResMed Operating Manual, Autoset Home System, 7 pp.
Resmed, Aug. 26, 1997, Mask frames, nasal cushions and headgear, web page, http://web/archive/org/web/199806111424/http:/www.resmed.com:80/maskframes/standar.htm., 3 pp.
Resmed, Feb. 12, 2001, Modular mask components and part numbers, https://web.archive.org/web/20010212075443/http:www.resmed.com:80/products/modular_components.htm, 1 p.
Photos of the Fisher and Paykel Healthcare Aclaim Mask, photos taken Oct. 6, 2023, 133 pp. (uploaded in 4 parts) The Fisher & Paykel Aclaim Mask has been publicly displayed, offered for sale and sold by the Applicant since at least 200.
Photos of the Healthdyne Soft Series Mask, photos taken Oct. 6, 2023, 45 pp. The Healthdyne Soft Series Mask has been publicly displayed, offered for sale and sold since at least 1993.
Letter to IP Australia dated Jun. 14, 2023 in Australian patent application No. 2021240146, 1 pp.
Opposition—Statement of Grounds and Particulars dated Jul. 18, 2023 in Australian patent application No. 2021240146, 20 pp.
Photos of the ResMed Activa Mask and Associated Packaging, photos taken Feb. 3, 2023, 120 pp.
The ResMed Mirage Activa Nasal Mask has been publicly displayed, offered for sale and sold by ResMed Pty Ltd since at least 2003 (Uploaded in 2 parts).
Photos of the ResMed Activa LT Mask and Associated Packaging, photos taken Feb. 3, 2023, 75pp. (uploaded in 5 parts) The ResMed Mirage Activa LT Nasal Mask has been publicly displayed, offered for sale and sold by ResMed Pty Ltd since at least 2008 (Uploaded in 5 parts).
Photos of the Respironics Comfort Curve and Associated Packaging, photos taken Feb. 3, 2023,143 pp. The Respironics Comfort Curve has been publicly displayed, offered for sale and sold by Respironics since at least 2005.
Photos of the Respironics Monarch Mini and Associated Packaging, photos taken Feb. 3, 2023, 152 pp. The Respironics Monarch Mini has been publicly displayed, offered for sale and sold by Respironics since at least 2000.
Statement of Grounds and Particulars dated Jun. 9, 2023 in Australian patent application No. 2021240146, 16 pp.
Statement of Grounds and Particulars dated Jul. 12, 2023 in Australian patent application No. 202173595, 19 pp.
Statutory Declaration for David John Palkon dated Sep. 7, 2023 in Australian patent application Nos. 2021240146 and 2021273595, 1879 pp. (uploaded in 4 parts).
Statutory Declaration for Melody Crinion dated Sep. 7, 2023 in Australian patent application Nos. 2021240146 and 2021273595, 98 pp.
Statutory Declaration of Robynne Lyndsay Sanders dated Sep. 7, 2023 in Australian patent application Nos. 2021240146 and 2021273595, 6566 pp (uploaded in 54 parts).
Photos of the Sullivan Bubble Mask, photos taken Feb. 3, 2023, 49 pp. (uploaded in 2 parts) TheSullivan Bubble Mask has been publicly displayed, offered for sale and sold by ResMed Pty Ltd (or its predecessor in title) since at least 1996.
Declaration of Jason Eaton dated Dec. 11, 2023 in the matter of Australian Patent ApplicationsNo. 2021240146 and 2021273595 in the name of Fisher & Paykel Healthcare Limited and Opposition by ResMed Pty Ltd, 227 pp.
European Examination Report, European Application 13828380.9, dated Jul. 27, 2018, 8 pp.
European Examination Report, European Application 13828380.9, dated Mar. 3, 2020, 8 pp.
European Extended Search Report dated Feb. 14, 2019 in patent application No. 18195537.8.
European extended search report dated Oct. 31, 2018 in patent application No. 18171619.2, 9 pp.
European Extended Search Report in patent application No. 10830251.4, dated Sep. 4, 2015, 7 pages.
European Extended Search Report in patent application No. 17179765.7, dated Dec. 11, 2017, 8 pages.
European Extended Search Report; dated Apr. 2, 2014; Application No. 09819444.2; 8 pages.
European Patent Office, Extended European Search Report, Application No. 18163847.9-1122, dated Jul. 23, 2018, in 7 pages.
European Search Report and Written Opinion in patent application No. 09746823.5, dated May 12, 2016, 12 pages.
European Search Report in patent application No. 11830981.4, dated Aug. 24, 2015; 6 pages.
European Search Report in patent application No. 191976761.1, dated Mar. 3, 2020, 10 pages.
European Summons to Attend Oral Proceedings and Written Opinion in patent application No. 09746823.5, dated Dec. 13, 2017, 7 pages.
Extended European Search Report in EP patent application No. 18178220.2, dated Sep. 21, 2018, 8 pp.
Extended Search Report; European Application No. 10774623.2; dated Sep. 8, 2015; 7 pages.
Great Britain combined search and examination report dated May 11, 2018 in patent application No. GB1805606.9. 3 pp.
Great Britain Combined Search and Examination Report in patent application No. GB1406401.8, dated May 7, 2014, 4 pages.
Great Britain Combined Search and Examination Report in patent application No. GB1406402.6, dated May 7, 2014, 6 pages.
Great Britain Combined Search and Examination Report in patent application No. GB1719334.3, dated Nov. 30, 2017, in 9 pages.
Great Britain examination report dated Jul. 20, 2018 in patent application No. GB1719334.3, 3 pp.
Great Britain examination report dated Jul. 5, 2018 in patent application No. GB1805606.9, 3 pp.
Great Britain examination report dated May 11, 2018 in patent application No. GB1805605, 1, 7 pp.
Great Britain examination report dated May 30, 2018 in patent application No. GB1719334.3, 4 pp.
Great Britain Examination Report in patent application No. GB1119385.1, dated May 9, 2013, 4 pages.
Great Britain examination report in patent application No. GB1501499.6, dated Jun. 1, 2017, in 8 pages.
Indian Examination Report dated Mar. 14, 2019 in patent application No. 8767/CHENP/2011. 6 pages.
Indian Examination Report in patent application No. 1431/KOLNP/2012. 7 pages.
Intention to Grant dated Nov. 22, 2021, in EP Application No. 18171619.2; in 55 pages.
International Preliminary Report on Patentability (IPRP), International application No. PCT/NZ2009/000219, dated Apr. 12, 2011,9 pages.
International Preliminary Report on Patentability and Written Opinion of the ISA; International Application No. PCT/ NZ2010/000229; dated May 22, 2012; 14 pages.
International Search Report and Written Opinion received for PCT Patent Application No. PCT/NZ2009/000072, mailed on Jul. 28, 2009, 12 pages.
International Search Report for application No. PCT/NZ2005/000062 dated May 27, 2005. 3 pages.
International Search Report for International Application No. PCT/NZ2007/000185, dated Oct. 31, 2007 in 3 pages.
International Search Report for International application No. PCT/NZ2014/000021, filed Feb. 21, 2014, 10 pages.
International Search Report, International Application No. PCT/NZ2009/000219, mailed Feb. 2, 2010, 3 pages.
International Search Report, PCT/NZ2010/000229, dated Mar. 18, 2011,8 pages.
International Search Report, PCT/NZ2011/000211, dated Feb. 17, 2012, 4 pages.
International Search Report; Application No. PCT/NZ2013/000138; dated Nov. 1, 2013; 7 pp.
Japanese Decision for Final Rejection dated Jul. 1, 2019 in patent application No. 2017-238259, 2 pp.
Japanese Examination Report in patent application No. 2012-510418, dated Feb. 10, 2014, 4 pages.

(56) References Cited

OTHER PUBLICATIONS

Japanese Examination Report in patent application No. 2012-538784, dated Aug. 25, 2014, 7 pages.
Japanese Examination Report in patent application No. 2015-098324, dated Jul. 22, 2015, 8 pages.
Japanese examination report in patent application No. 2015-526496, dated Apr. 17, 2017, in 13 pages.
Japanese Examination Report in patent application No. 2015-526496, dated Feb. 28, 2018, 2 pp.
Japanese Examination Report in patent application No. 2017-040092, dated Feb. 5, 2018. 4 pages.
Japanese Examination Report; dated Jul. 22, 2015; Application No. 2015-098324; 8 pages.
Japanese notification of reason for rejection in patent application No. 2012-538784, dated Aug. 5, 2015, 10 pp.
Japanese office action dated Sep. 1, 2019 in patent application No. 2018-188040. 10 pages.
Japanese Office Action; Application No. 2012-538784; dated Jul. 25, 2016; 4 pages.
Japanese Official Action dated Sep. 3, 2018 in patent application No. 2017-238259. 8 pages.
Japanese Pretrial Examination Report dated Jan. 7, 2020 in patent application No. 2017-238259. 4 pages.
Office Action in corresponding Indian Patent Application No. 5250/KOLNP/2008, dated May 23, 2017, in 8 pages.
Office Action; Canadian Application No. 2890556; dated Jan. 27, 2016; 3 pages.
Office Action; European Application No. 07808683.2; dated Jul. 8, 2015; 8 pages.
Scheduling Order dated Jul. 16, 2019 in IPR2019-00180, 12 pp.
Third Office Action; Chinese Application No. 201080061122.1; dated Apr. 1, 2016; 5 pages.
UK Search and Examination Report; Mar. 14, 2013; Application No. GB1210075.6; 2 pages.
Written Opinion of the international Searching Authority, PCT/NZ2013/000139, dated Nov. 1, 2013. 5 pages.
Written Opinion, PCT/NZ2011/00021, dated Feb. 17, 2012, 7 pages.
Written Opinion; PCT/NZ2011/000211; dated Feb. 172012; 7 pages.

* cited by examiner

BREATHING ASSISTANCE APPARATUS

PRIORITY, INCORPORATION BY REFERENCE

This application is a continuation of U.S. patent application Ser. No. 17/816,275, filed Jul. 29, 2022 and issuing as U.S. Pat. No. 11,766,535, which is a continuation of U.S. patent application Ser. No. 17/568,186, filed Jan. 4, 2022, now U.S. Pat. No. 11,559,650, which is a continuation of U.S. patent application Ser. No. 16/384,218, filed Apr. 15, 2019, now U.S. Pat. No. 11,247,013, which is a continuation of both U.S. patent application Ser. No. 14/977,083, filed Dec. 21, 2015, now U.S. Pat. No. 10,272,218, and of U.S. patent application Ser. No. 15/425,937, filed Feb. 6, 2017, now U.S. Pat. No. 10,835,702. Both U.S. patent application Ser. Nos. 14/977,083 and 15/425,937 claim priority to U.S. patent application Ser. No. 13/877,903, filed May 30, 2013, now U.S. Pat. No. 9,561,338, which claims priority to international Patent App. No. PCT/NZ2011/000211, filed Oct. 7, 2011, which claims benefit of U.S. Provisional Patent App. No. 61/391,527, filed Oct. 8, 2010. All of the above, and any and all applications for which a foreign or domestic priority claim is identified in the Application Data Sheet as filed with the present application, are hereby incorporated by reference under 37 CFR § 1.57, for all that each contains, for all purposes.

BACKGROUND

Field

The present invention generally relates to patient interfaces. More particularly, the present invention relates to such interfaces particularly though not solely for use in delivering CPAP therapy to patients suffering from obstructive sleep apnoea (OSA).

Related Art

In the art of respiration devices, there are a variety of respiratory masks that cover the nose and/or mouth of a human user in order to provide a continuous seal around the nasal and/or oral areas of the face such that gas may be provided at positive pressure within the mask for consumption by the user. The uses for such masks range from high altitude breathing (i.e., aviation applications) to mining and firefighting applications, to various medical diagnostic and therapeutic applications.

Such respiratory masks should provide an effective seal against the user's face to reduce the likelihood of leakage of the gas being supplied. Commonly, in prior mask configurations, a good mask-to-face seal has been attained in many instances only with considerable discomfort for the user. This problem is prevalent in those applications, especially medical applications, in which the user wears a mask or patient interface continuously for hours or perhaps even days. In such situations, the user may not tolerate the mask for long durations and optimum therapeutic or diagnostic objectives thus will not be achieved, or will be achieved with great difficulty and considerable user discomfort.

To aid with user comfort, masks can be provided in a range of different sizes. A user will find one particular size in the available range of sizes most suitable for providing an effective seal and a comfortable fit. A single mask frame can be provided to which a range of different sized seals may be fitted. A user chooses the most suitably sized seal from the available range (e.g., the user chooses one size from small, medium, large and extra large) and attaches that seal to the mask frame for use.

A further example of a way in which differently sized users are accommodated is the nasal mask range disclosed in US2010/0006101, the entire contents of which are hereby incorporated by reference herein. As shown in FIG. 1 of this application, three different sized mask bodies 430 and correspondingly sized seal assemblies 440 are provided. A user may select the most suitably sized frame and corresponding seal assembly for use. Various components of the nasal mask disclosed in US2010/0006101 are described below with reference to FIGS. 2 to 6.

The mask assembly 402 comprises a mask body 430 and a mask seal assembly 440. The mask body 430 provides the overall structural support for the mask assembly, and provides a clip type fitting 433 for attaching the mask assembly 402 to headgear 421. The mask body includes a forehead support 431 to which the headgear is also attached.

A rear side of the mask body 430 interfaces to the seal assembly 440. The seal assembly 440 provides a sealing interface against a user's face in use.

The mask body 430 has an inlet for receiving a flow of respiratory gases and exhaust holes 425 to allow exhaled breath to be vented from the mask assembly. The mask body forms an internal cavity to which respiratory gases are supplied via the inlet. The inlet comprises a tubular projection 422 extending from a front side 471 of the mask body 430. A connector 423 connects to the inlet and swivels with respect to the mask body 430, for connecting a supply conduit to the mask body.

The seal assembly 440 comprises a flexible seal 443 attached to a relatively rigid plastic clip 442. The flexible seal 443 is over-moulded to the plastic clip 442 so that the seal assembly 440 forms a single item of the mask assembly 402. The plastic clip has a series of holes 446 around its perimeter. During manufacture, overmoulding of the seal to the clip causes the seal material to flow through the series of holes 446. During manufacture, the seal material is cured. Once cured, the seal 443 is mechanically linked to the plastic clip 442 via holes 446, providing a mechanical joint between the clip and the seal. The holes 446 are located through a raised ridge 445 running around the inside perimeter of the clip.

The clip 442 releasably attaches to the mask body in a 'clip' or 'snap' type engagement. A series of bumps 448, or raised portions, on the mask body 430 interact with corresponding recesses 447 on the clip 442, to hold the clip 442 in place on the body 430. As the clip 442 attaches to the mask body, interference between the clip and each mask body bump 448 causes the clip or the mask body, or both, to deflect to a deflected condition until each bump 448 reaches a corresponding recess 447. Once the clip has been fully engaged with the body, each bump 448 locates within a corresponding recess 447, and the clip or body, or both un-deflect from the deflected condition to an un-deflected or partially deflected condition, the parts being clipped or snapped together in a fully engaged position.

The clip 442 preferably has a relatively long lead in, or ramped profile 449, leading to the clip recess 447. This lead in section extends the full inside perimeter length of the clip 442. The lead-in section assists with the attachment of the clip to the mask body. The clip 442 or mask body 430, or both, are gradually deflected over the length of the lead-in section until the apex of the lead-in section and each mask body bump 448 pass each other. Once the bumps 448 have passed over the lead-in section, the bumps 448 locate within each corresponding recess 447, such that there is little or no interference between the two parts 430 and 442. The two parts un-deflect in a relatively sudden snap action compared to the gradual deflection caused by the lead in section 449 during engagement.

The face seal assembly 440 includes at least one wing portion 444 to assist a user to disengage the face seal assembly from the mask body. The wing portions 444 provide a gripping flange to pull the clip 442 away from the mask body 430.

The nasal mask includes a cushion 441. Cushion 441 is provided around the periphery of the mask, and is surrounded by the seal assembly 440. The cushion 441 provides support to the seal 443 to achieve an effective seal onto the face of the user to reduce the likelihood of leakage.

One end 462 of the mask cushion is shaped to match the shape of the seal in contact with the user's face, and an opposite end 463 is shaped to match the mask body. The cushion includes a raised bridge 465 in the nasal bridge region. The raised bridge 465 can also be described as a cut out section made in the cushion, the cut out being on the mask body end 463 of the cushion. As the raised bridge 465 is unsupported by the mask body 430, it is much more flexible and results in less pressure on the nasal bridge of the patient.

The cushion 441 is located around the outer periphery of the mask body, contacting the mask body except for in the raised bridge portion 465 of the cushion. The cushion is located in a generally triangular cavity 466, the cavity continuing around the periphery of the body, terminating at each side of the nose bridge region 467 of the mask, where the raised bridge portion 465 of the cushion does not contact the mask body 430. The cavity 466 is generally formed by two spaced apart walls 476 and 477. The cushion 441 is a separate item, the seal assembly 440 fitting in place over the cushion to hold it in place within the mask assembly 402.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

SUMMARY

An object of the present invention is to provide a patient interface which goes some way to overcoming disadvantages in the prior art or which will at least provide the users with a useful choice.

In one aspect, the present invention broadly consists in a mask assembly for use as part of an apparatus for supplying a flow of respiratory gases to a user, comprising:
 a mask body having an inlet through which said flow of respiratory gases are provided to the interior of said mask body, the inlet adapted to be connected to a gases conduit,
 a mask seal assembly comprising a seal of flexible material and a clip of rigid material,
 the seal having a first side and a second side, the first side of the seal being shaped to approximately match the contours of a user's face and in use substantially seal against a user's face, the second side attached to said clip,
 the clip providing an interface extending substantially the full perimeter or periphery of the mask seal assembly for releasably attaching the mask seal assembly to the mask body, and
 wherein the clip comprises a bridging portion spanning outwards from the perimeter or periphery of the mask body to space at least a portion of the second side of the seal outwards from the perimeter or periphery of the mask body.

Preferably the mask assembly comprises an inner cushion located between the clip and the first side of the seal.

Preferably the inner cushion is located between the bridging portion of the clip and the first side of the seal.

Preferably the clip comprises a channel in the bridging portion, a first side of the inner cushion in use supporting the first side of the seal, and a second side of the inner cushion being received in the channel.

Preferably the seal is attached to a first side of the clip and a second side of the clip releasably attaches to the mask body, and the bridging portion spans between the first and second sides of the clip.

Preferably the seal assembly comprises a second seal of flexible material attached to the second side of the clip for forming a seal between the mask seal assembly and the mask body.

Preferably the bridging portion and the seal are sized according to one of a series of sizes, each one of the series of sizes suitable for sealing against a differently sized user's face.

Preferably the mask body is adapted for use with a plurality of the seal assemblies, at least one said seal assembly having a said bridging portion, each said seal assembly having a said seal sized according to one of a series of sizes, each one of the series of sizes suitable for sealing against a differently sized user's face, and the second side of the clip of each said seal assembly being the same or similar to be releasably attached to the mask body.

Preferably the seal and the second seal are integrally formed and joined together across the bridging portion.

Preferably the seal and the second seal are integrally formed and joined together across the bridging portion via a runner across or through the bridging portion.

Preferably the mask assembly comprises an inner cushion located between the mask body and the first side of the seal.

Preferably the mask assembly comprises a channel in the mask body, a first side of the inner cushion in use supporting the first side of the seal, and a second side of the inner cushion being received in the channel in the mask body.

Preferably the bridging portion has an outward dimension that is the same or similar around the perimeter or periphery of the mask body.

Preferably the bridging portion has an outward dimension that varies around the perimeter or periphery of the clip.

Preferably the outward dimension of the bridging portion is larger at a bottom portion of the seal assembly and smaller at an upper portion or nasal bridge region of the seal assembly.

Preferably the bridging portion tapers from a first outward dimension in the bottom portion of the mask assembly to a second outward dimension in the upper portion or nasal bridge region of the mask assembly.

Preferably each said seal assembly in the said plurality of seal assemblies has a bridging portion with a first outward dimension in the bottom of the mask assembly and a second outward dimension in the upper portion of the mask assembly and the first outward dimension is greater than the second outward dimension, and the second outward dimension of each said seal assembly is the same or similar, and the first outward dimension of each said seal assembly is different to the first outward dimension of the other said seal assemblies in said plurality of seal assemblies, the first outward dimension of each said seal assembly sized to be suitable for sealing against a differently sized user's face.

Preferably the bridging portion extends rearward away from a front of the mask body towards a user's face in use.

Preferably the mask body is adapted for use with a plurality of the seal assemblies, at least one said seal assembly having a said bridging portion, each said seal assembly having a seal of a different type comprising one of a cannula seal, a nasal seal, a mouth seal and a full face seal, and the second side of the clip of each said seal assembly being the same or similar to be releasably attached to the mask body.

Preferably the mask seal assembly releasably attaches to a rear perimeter of the mask body.

Preferably the rear perimeter of the mask body defines an area being more than ten times the area of the mask body inlet.

Preferably the bridging portion spaces the second side of the seal outwards from the perimeter or periphery of the mask body by at least 10 mm.

Preferably the mask body defines a hollow space for receiving or covering a user's nose or mouth or both.

In another aspect, the present invention broadly consists in a mask package comprising:
 a mask body having an inlet through which a flow of respiratory gases are provided to the interior of the mask body, the inlet adapted to be connected to a gases conduit,
 a first seal assembly comprising:
 a first seal of a flexible material and a first clip of a rigid material, the first seal having a first side and a second side, the first side of the first seal being shaped to approximately match the contours of a user's face and in use substantially seal against a user's face, said second side of said first seal attached to said first clip, the first clip providing an interface extending substantially the full perimeter or periphery of the first seal assembly, the second side of the first seal attached to a first side of the first clip and a second side of the first clip for releasably attaching the first seal assembly to the mask body,
 a second seal assembly comprising:
 a second seal of a flexible material and a second clip of a rigid material, the second seal having a first side and a second side, the first side of the second seal being shaped to approximately match the contours of a user's face and in use substantially seal against a user's face, said second side of said second seal attached to said second clip,
 the second clip providing an interface extending substantially the full perimeter or periphery of the second seal assembly, the second side of the second seal attached to a first side of the second clip and a second side of the second clip for releasably attaching the second seal assembly to the mask body,
 wherein the first clip or the second clip or both comprises a bridging portion spanning outwards from the perimeter or periphery of the mask body to space at least a portion of the second side of the first or second seal outwards from the perimeter or periphery of the mask body when the first or second seal assembly is attached to the mask body, and the first side of the first clip being comparatively different to the first side of the second clip, and the first seal being comparatively different to the second seal.

Preferably the mask package comprises a first inner cushion for use with the first seal assembly and a second inner cushion for use with the second seal assembly.

Preferably the first seal assembly attached to the mask body, the first inner cushion is located between the first clip and the first side of the first seal, or with the second seal assembly attached to the mask body, the second inner cushion is located between the second clip and the first side of the second seal.

Preferably the first seal assembly attached to the mask body, the first inner cushion is located between the bridging portion of the first clip and the first side of the first seal, or with the second seal assembly attached to the mask body, the second inner cushion is located between the bridging portion of the second clip and the first side of the second seal.

Preferably the bridging portion of the first clip of the first seal assembly has a channel for receiving the first inner cushion, or/and the bridging portion of the second clip of the second seal assembly has a channel for receiving the second inner cushion.

Preferably the bridging portion of the first clip of the first seal assembly has an outward dimension that varies around the perimeter of the first clip, or the bridging portion of the second clip of the second seal assembly has an outward dimension that varies around the perimeter of the first clip.

Preferably the bridging portion of the first clip of the first seal assembly has a larger outward dimension at the bottom of the first seal assembly compared to the outward dimension at the top or nasal bridge region of the first seal assembly, and/or the bridging portion of the second clip of the second seal assembly has a larger outward dimension at the bottom of the second seal assembly compared to the outward dimension at the top or nasal bridge region of the second seal assembly.

Preferably the bridging portion of the second clip of the second seal assembly has a larger outward dimension at the bottom of the second seal assembly compared to the bridging portion of the first clip of the first seal assembly, the second seal of the second seal assembly being larger than the first seal of the first seal assembly.

Preferably the bridging portion of the first clip of the first seal assembly and the bridging portion of the second clip of the second seal assembly have the same or a similar outward dimension in the nasal bridge region of the clip.

Preferably the first side of the second seal has a longer perimeter length than the first side of the first seal.

Preferably a mask assembly comprising the mask body and the first seal assembly has an internal cavity having a first depth, and a mask assembly comprising the mask body and the second seal assembly has an internal cavity having a second depth, the second depth being greater than the first depth.

Preferably the bridging portion of the second clip of the second seal assembly extends rearward away from the general plane of the mask body when the second seal assembly is attached to the mask body.

Preferably the first seal assembly comprises a seal of flexible material attached to the second side of the first clip for forming a seal between the first mask seal assembly and the mask body, and/or
 the second seal assembly comprises a seal of flexible material attached to the second side of the second clip for forming a seal between the second mask seal assembly and the mask body.

Preferably the first seal of the first seal assembly and the seal on the second side of the first clip of the first seal assembly are integrally formed and joined together across the bridging portion of the first clip, and/or
the second seal of the second seal assembly and the seal on the second side of the second clip of the second seal assembly are integrally formed and joined together across the bridging portion of the second clip.

Preferably a mask assembly comprising the mask body and the first seal assembly or the second seal assembly is a nasal mask or a full face mask.

Preferably the first side of the second clip has a longer perimeter length than the first side of the first clip, the second seal being larger than the first seal.

Preferably the first side of the second seal has a longer perimeter length than the first side of the first seal.

Preferably the first and second seals are different types of seals, the first and second seals being one of a cannula seal, a nasal seal, a mouth seal and a full face seal.

Preferably the first mask seal assembly and the second mask seal assembly releasably attach to a rear perimeter of the mask body.

Preferably the rear perimeter of the mask body defines an area being more than ten times the area of the mask body inlet.

Preferably the bridging portion of the first clip spaces the second side of the first seal outwards from the perimeter or periphery of the mask body by at least 10 mm, or the bridging portion of the second clip spaces the second side of the second seal outwards from the perimeter or periphery of the mask body by at least 10 mm.

Preferably the mask body defines a hollow space for receiving or covering a user's nose or mouth or both.

In another aspect, the present invention broadly consists in a mask assembly for use as part of an apparatus for supplying a flow of respiratory gases to a user, comprising:
a mask body having an inlet through which said flow of respiratory gases are provided to the interior of said mask body, the inlet adapted to be connected to a gases conduit,
a mask seal assembly comprising a seal of a flexible material and a clip of a rigid material,
said seal having a first side and a second side, the first side of said seal being shaped to approximately match the contours of a user's face and in use substantially seal against a user's face, said second side attached to said clip,
said clip providing an interface extending substantially the full perimeter or periphery of the mask seal assembly for releasably attaching the mask seal assembly to the mask body, and
an inner cushion located between the clip and said first side of the seal.

Preferably the clip comprises a bridging portion spanning outwards from the perimeter or periphery of the mask body to space at least the second side of the seal outwards from the perimeter or periphery of the mask body.

Preferably the inner cushion is located between the bridging portion and the first side of the seal.

Preferably the clip comprises a channel in the bridging portion, a first side of the inner cushion in use supporting the first side of the seal, and a second side of the inner cushion being received in the channel.

Preferably the seal is attached to a first side of the clip and a second side of the clip releasably attaches to the mask body, and the bridging portion spans between the first and second sides of the clip.

Preferably the seal assembly comprises a second seal of flexible material attached to the second side of the clip for forming a seal between the mask seal assembly and the mask body.

Preferably the bridging portion and said seal are sized according to one of a series of sizes, each one of the series of sizes suitable for sealing against a differently sized user's face.

Preferably the mask body is adapted for use with a plurality of said seal assemblies, at least one said seal assembly having a said bridging portion, each said seal assembly having a said seal sized according to one of a series of sizes, each one of the series of sizes suitable for sealing against a differently sized user's face, and said second side of the clip of each said seal assembly being the same or similar to be releasably attached to the mask body.

Preferably the seal and the second seal are integrally formed and joined together across the bridging portion.

Preferably the seal and the second seal are integrally formed and joined together across the bridging portion via a runner across or through the bridging portion.

Preferably the mask assembly comprises an inner cushion located between the mask body and said first side of the seal.

Preferably the mask assembly comprises a channel in the mask body, a first side of the inner cushion in use supporting the first side of the seal, and a second side of the inner cushion being received in the channel in the mask body.

Preferably the bridging portion has an outward dimension that is the same or similar around the perimeter or periphery of the mask body.

Preferably the bridging portion has an outward dimension that varies around the perimeter or periphery of the clip.

Preferably the outward dimension of the bridging portion is larger at a bottom portion of the seal assembly and smaller at an upper portion or nasal bridge region of the seal assembly.

Preferably the bridging portion tapers from a first outward dimension in the bottom portion of the mask assembly to a second outward dimension in the upper portion or nasal bridge region of the mask assembly.

Preferably each said seal assembly in the said plurality of seal assemblies has a bridging portion with a first outward dimension in the bottom of the mask assembly and a second outward dimension in the upper portion of the mask assembly and the first outward dimension is greater than the second outward dimension, and the second outward dimension of each said seal assembly is the same or similar, and the first outward dimension of each said seal assembly is different to the first outward dimension of the other said seal assemblies in said plurality of seal assemblies, the first outward dimension of each said seal assembly sized to be suitable for sealing against a differently sized user's face.

Preferably the bridging portion extends rearward away from a front of the mask body towards a user's face in use.

Preferably the mask body is adapted for use with a plurality of the seal assemblies, at least one said seal assembly having a said bridging portion, each said seal assembly having a seal of a different type comprising one of a cannula seal, a nasal seal, a mouth seal and a full face seal, and the second side of the clip of each said seal assembly being the same or similar to be releasably attached to the mask body.

Preferably the mask seal assembly releasably attaches to a rear perimeter of the mask body.

Preferably the rear perimeter of the mask body defines an area being more than ten times the area of the mask body inlet.

Preferably the bridging portion spaces the second side of the seal outwards from the perimeter or periphery of the mask body by at least 10 mm.

Preferably the mask body defines a hollow space for receiving or covering a user's nose or mouth or both.

In another aspect, the present invention broadly consists in a mask seal assembly for use as part of an apparatus for supplying a flow of respiratory gases to a user, comprising:

a seal of flexible material and a clip of rigid material,
the seal having a first side and a second side, the first side of the seal being shaped to approximately match the contours of a user's face and in use substantially seal against a user's face, the second side attached to said clip,
the clip providing an interface extending substantially the full perimeter or periphery of the seal assembly, the clip having a first side and a second side, the second side of the seal being attached to the first side of the clip, and the second side of the clip for releasably attaching the mask seal assembly to a mask body,
wherein the clip comprises a bridging portion spanning between the first and second sides of the clip to space at least a portion of the second side of the seal outwards from the perimeter or periphery of the second side of the clip.

Preferably the clip comprises a channel in the bridging portion for receiving an inner cushion for supporting the first side of the seal in use.

Preferably the seal assembly comprises a second seal of flexible material attached to the second side of the clip for forming a seal between the mask seal assembly and a mask body.

Preferably the bridging portion and the seal are sized according to one of a series of sizes, each one of the series of sizes suitable for sealing against a differently sized user's face.

Preferably the seal and the second seal are integrally formed and joined together across the bridging portion.

Preferably the seal and the second seal are integrally formed and joined together across the bridging portion via a runner across or through the bridging portion.

Preferably the bridging portion has an outward dimension that is the same or similar around the perimeter or periphery of the mask seal assembly.

Preferably the bridging portion has an outward dimension that varies around the perimeter or periphery of the clip.

Preferably the outward dimension of the bridging portion is larger at a bottom portion of the seal assembly and smaller at an upper portion or nasal bridge region of the seal assembly.

Preferably the bridging portion tapers from a first outward dimension in the bottom portion of the mask assembly to a second outward dimension in the upper portion or nasal bridge region of the mask assembly.

Preferably the bridging portion extends rearward away from a front of a mask body to which the mask assembly is attached in use and towards a user's face in use.

Preferably the mask seal assembly is adapted to releasably attach to a rear perimeter of a mask body defining a hollow space for receiving or covering a user's nose or mouth or both and having an inlet through which the flow of gases are provided to the interior of the mask body.

Preferably the rear perimeter of the mask body defines an area being more than ten times the area of the mask body inlet.

Preferably the bridging portion spaces the second side of the seal outwards from the perimeter or periphery of the second side of the clip by at least 10 mm.

The term "comprising" is used in the specification and claims, means "consisting at least in part of." When interpreting a statement in this specification and claims that includes "comprising", features other than that or those prefaced by the term may also be present. Related terms such as "comprise" and "comprises" are to be interpreted in the same manner. The invention consists in the foregoing and also envisages constructions of which the following gives examples.

For purposes of summarizing the invention and the advantages achieved over the prior art, certain objects and advantages of the invention have been described above and as further described below. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

Preferred forms of the present invention will now be described with reference to the accompanying drawings. The appended drawings are schematic, not necessarily drawn to scale, unless otherwise indicated, and are meant to illustrate and not to limit embodiments of the invention.

DETAILED DESCRIPTION

It will be appreciated that the mask assembly as described in the preferred embodiment of the present invention can be used in respiratory care generally or with a ventilator, but will now be described below with reference to use in a humidified Continuous Positive Airway Pressure (CPAP) system. It will also be appreciated that the present invention can be applied to various forms of mask assembly including, but not limited to, nasal masks and full face masks that cover both the user's nose and mouth.

Figure 7:
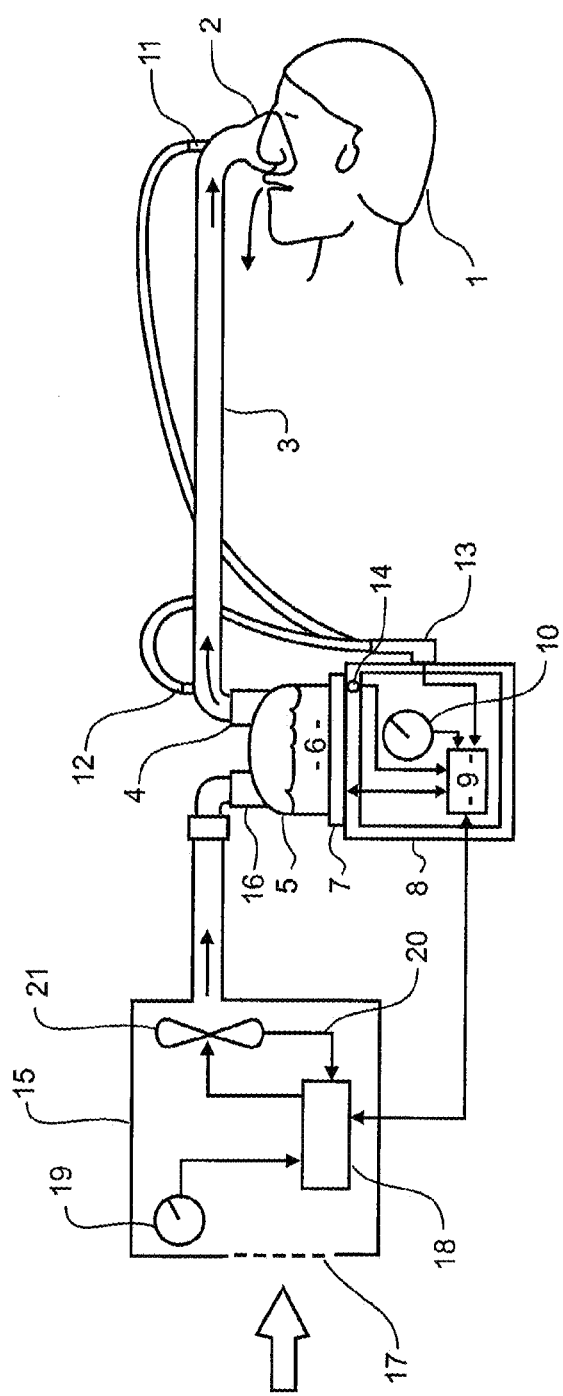
FIG. 7 is a block diagram of a humidified continuous positive airway pressure system as might be used in conjunction with the mask assembly of the present invention.

With reference to FIG. 7 a humidified CPAP system is shown in which a patient 1 is receiving humidified and pressurised gases through a patient interface 2 connected to a supply conduit 3. It should be understood that CPAP is used generically and includes a range of variants including VPAP (Variable Positive Airway Pressure) and BiPAP (Bi-level Positive Airway Pressure) and numerous other forms of respiratory therapy.

Supply conduit 3 is connected to the outlet 4 of a humidification chamber 5 that contains a volume of water 6. Supply conduit 3 may contain a heater or heater wires (not shown) which heat the walls of the conduit or the gases in the conduit to reduce condensation of humidified gases within the conduit. Humidification chamber 6 is preferably formed from a plastics material. The contents of the chamber are heated by a heater. For example the chamber may have a highly heat conductive base (for example an aluminium base) which is in direct contact with a heater plate 7 of humidifier 8. Humidifier 8 is provided with control means or electronic controller 9 which may comprise a microprocessor based controller executing computer software commands stored in associated memory.

Figure 1:
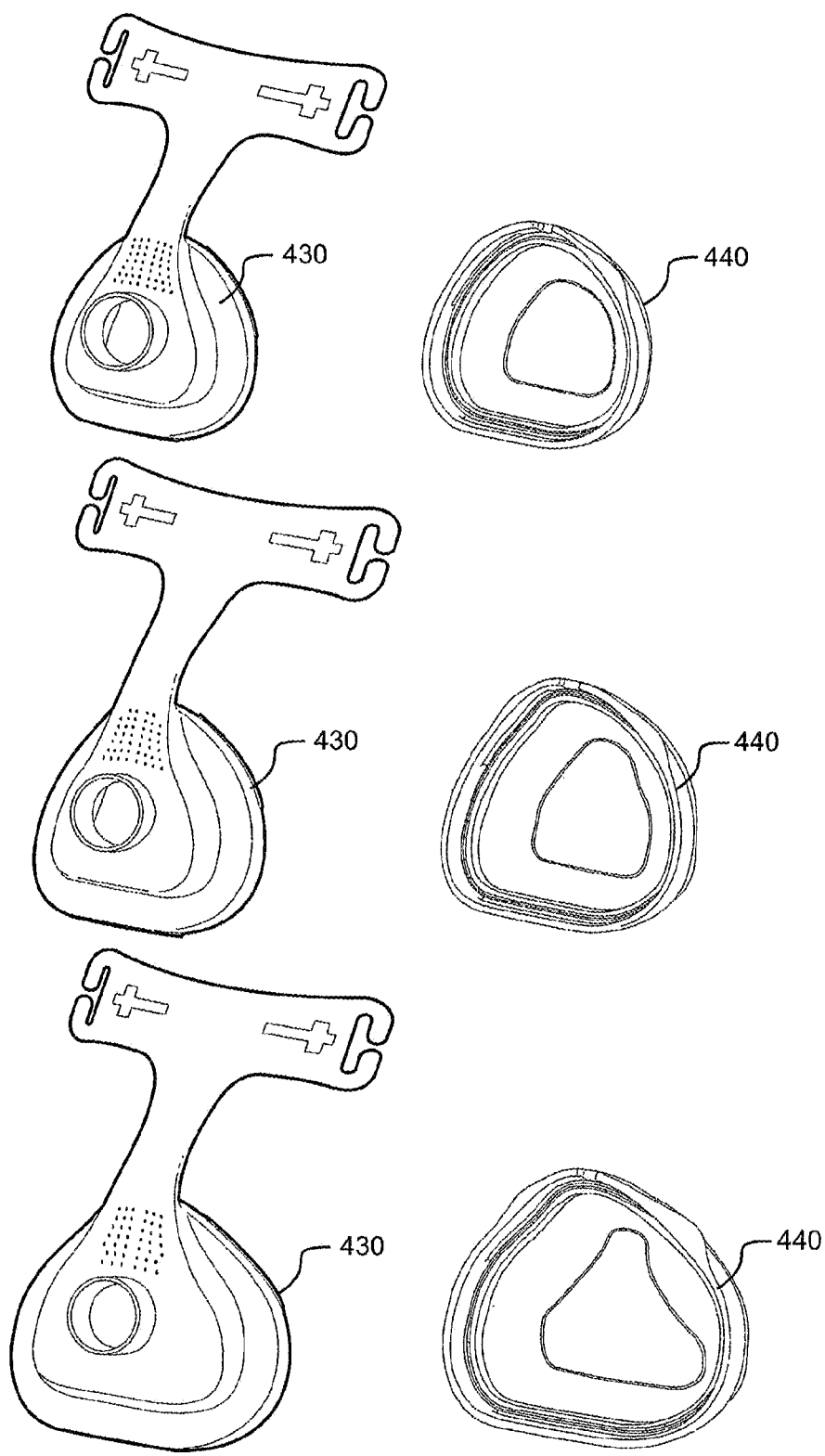
FIG. 1 illustrates three differently sized prior art mask frames and corresponding seal assemblies.
Figure 2:
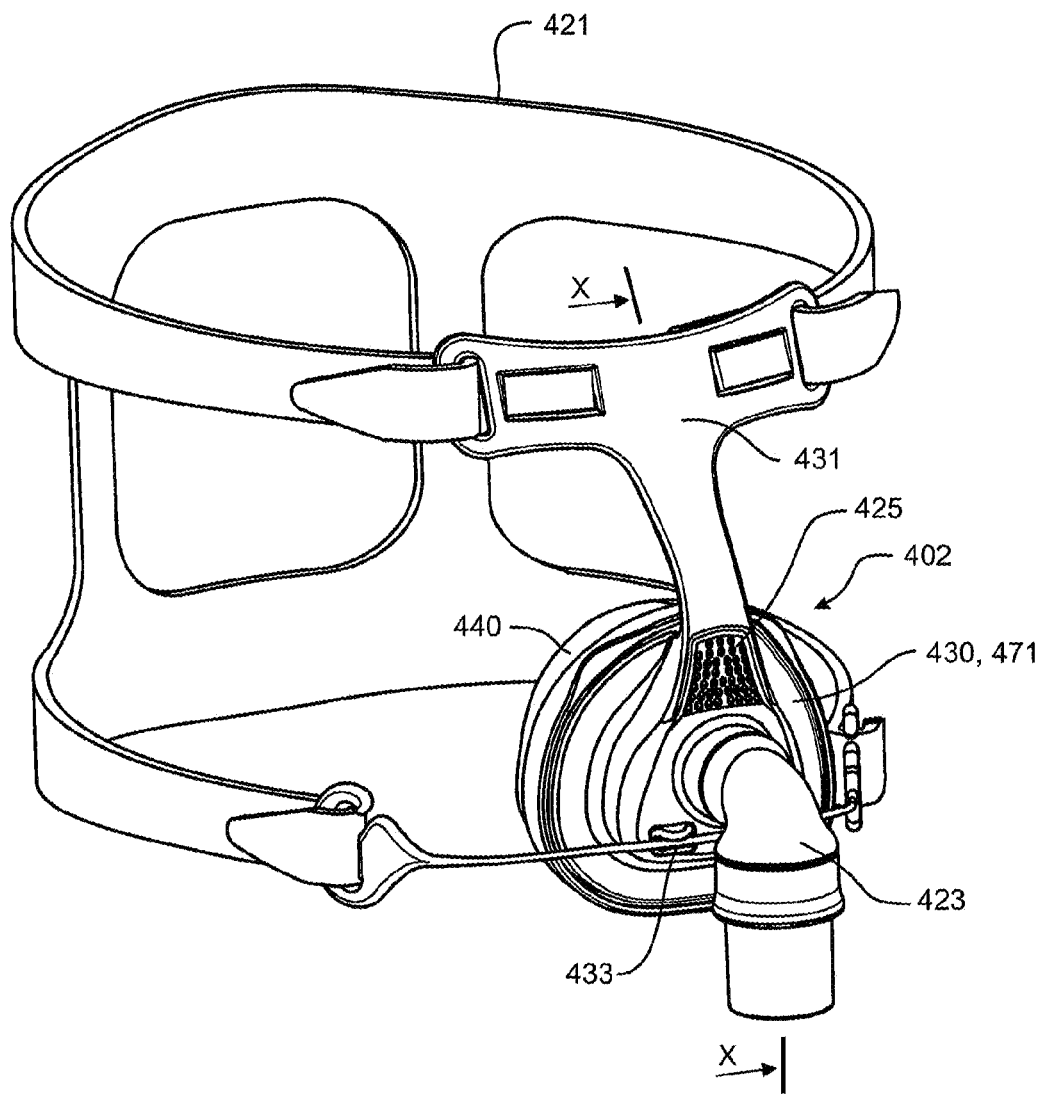
FIG. 2 is a perspective view of the nasal mask of FIG. 1.
Figure 3:
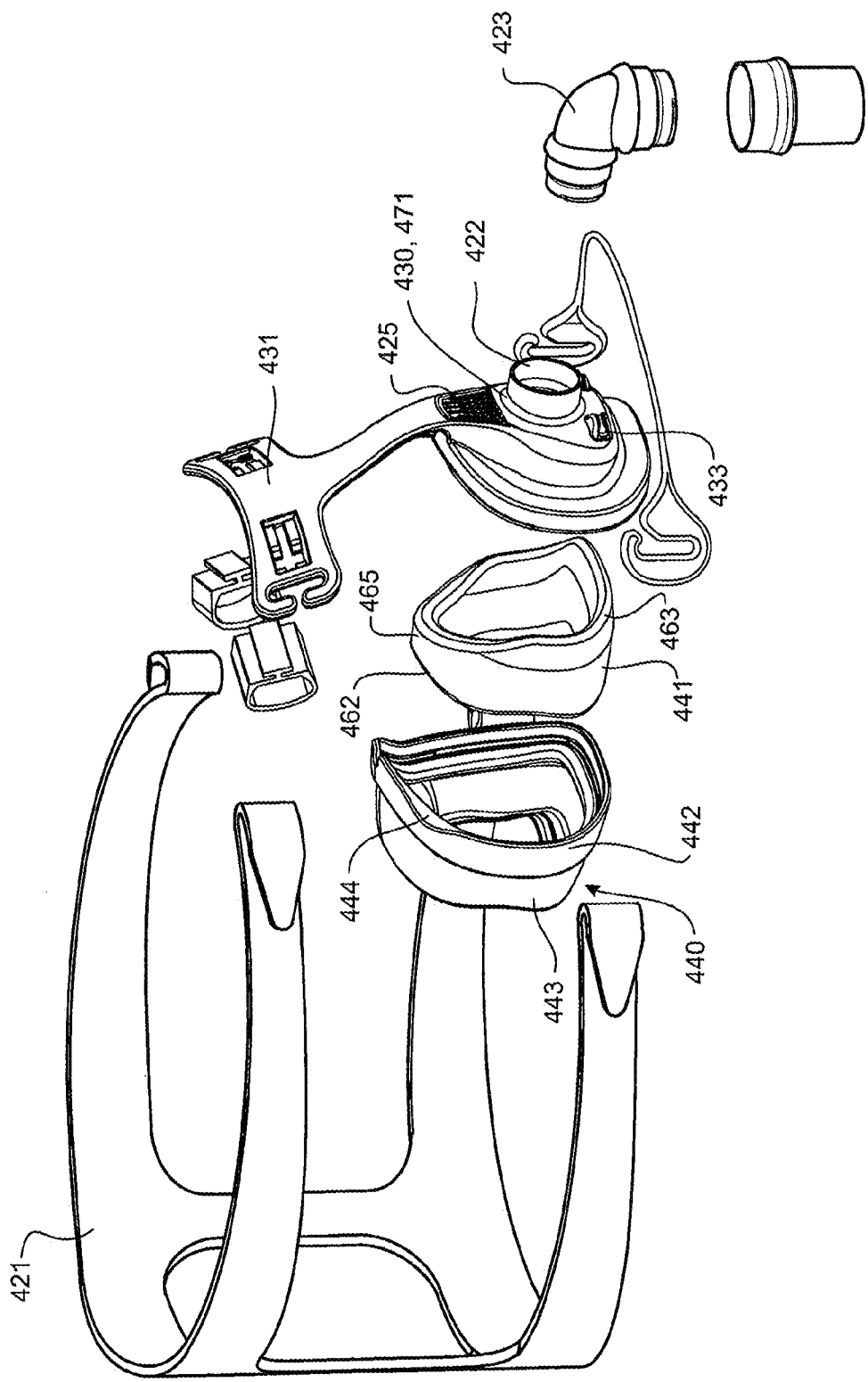
FIG. 3 is an exploded view of the nasal mask of FIG. 1.

Controller 9 receives input from sources such as a user interface or dial 10 through which a user of the device may, for example, set a value (e.g., a preset or predetermined value) of humidity or temperature of the gases to be supplied. The controller may also receive input from other sources; for example temperature and/or flow velocity sensors 11 and 12 through connector 13 and heater plate temperature sensor 14. In response to the user set humidity or temperature value input via dial 10 and the other inputs, controller 9 determines when (or to what level) to energise heater plate 7 to heat the water 6 within humidification chamber 5. As the volume of water 6 within humidification chamber 5 is heated, water vapour begins to fill the volume of the chamber above the water's surface and is passed out of the humidification chamber 5 outlet 4 with the flow of gases (for example air) provided from a gases supply means or blower 15 which enters the chamber through inlet 16. Exhaled gases from the patient's mouth are passed directly to ambient surroundings in FIG. 1.

Blower 15 is provided with variable pressure regulator or a variable speed fan 21. The fan draws air or other gases through blower inlet 17. The speed of the variable speed fan 21 is controlled by electronic controller 18 (or alternatively the function of controller 18 could carried out by controller 9) in response to inputs from controller 9.

Mask Assembly

Figure 8:
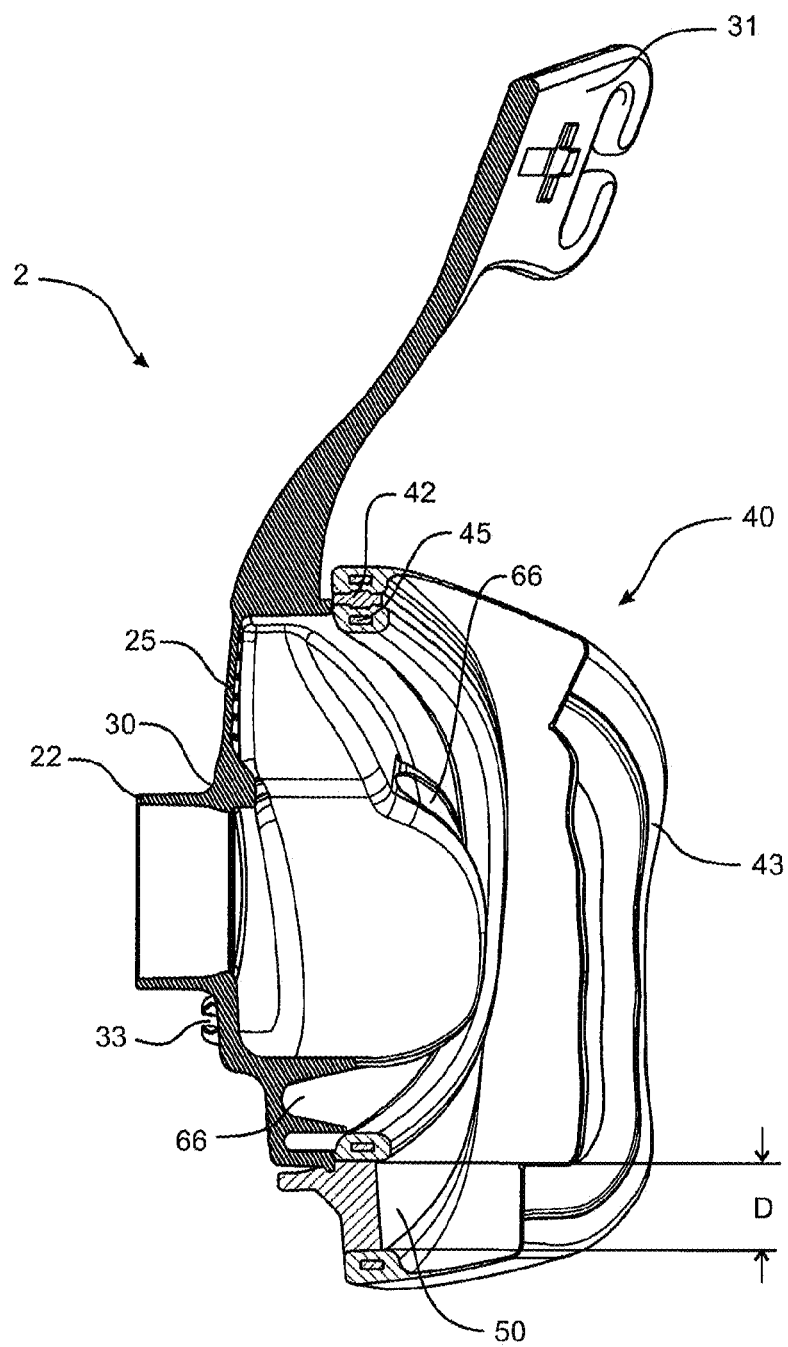
FIG. 8 is a cross sectional view of a mask assembly according to one embodiment of the present invention.

A mask assembly 2 according to the present invention is described with reference to FIGS. 8 to 13. FIG. 8 shows a mask comprising a mask body 30. The mask body includes an inlet 22 for receiving a flow of gases into the mask assembly. The mask body preferably includes features for securing the mask assembly in position on the user's face. For example, the embodiment of FIG. 8 includes a forehead rest 31 to assist with correct placement of the mask assembly against the user's face, and a clip 33 for attachment to headgear. Headgear may also be attached to features of the forehead rest. The mask body may include other known features, for example vent holes 25 for venting expired gases and air, and a channel 66 for receiving an inner cushion (not shown) for supporting the seal 43.

A seal assembly 40 comprising a seal 43 of a flexible material and clip 42 of a rigid material is attached to a rear side of the mask body. A first side of the flexible seal contacts a user's facial features in use. A second side of the flexible seal is attached to the clip. The seal assembly is releasably attached to the mask body 30 by the clip. Preferably the clip extends substantially the full perimeter of the mask seal assembly. The clip is rigid compared to the seal material and provides a convenient interface for releasably attaching the flexible seal to the mask body. For example, the clip is manufactured from polycarbonate, ABS, nylon, acetyl or other similar rigid plastic. Alternatively the clip may be made from a high Shore A hardness silicone. For example, a silicone with a Shore A hardness of 90 may provide sufficient rigidity. The clip and mask body may be manufactured from the same material type. The seal is formed from rubber or other suitable flexible, resilient material. Preferable the seal is formed from silicone with a Shore-A hardness of less than 60. Preferably the seal is made from silicone with a Shore A hardness of 20-40.

From the above mentioned materials, the difference in rigidity of the clip material (rigid) and the seal material (flexible) will be appreciated. For example, polycarbonate has a Young's modulus of approximately 2 GPa, whereas the Young's modulus of a rubber or other suitable material for use as the flexible seal is in the order of 1 to 5 MPa.

The seal generally provides a flexible perimeter about the perimeter or periphery of the mask body. The seal surrounds an opening to the inside of the mask assembly. A nasal mask assembly seals against a user's face around the user's nose, the seal opening covering the user's nose. A full face mask seals against a user's face around the users nose and mouth, the seal opening covering both the user's nose and mouth.

The clip has a bridging portion 50 that spans outwards from the perimeter or periphery of the mask body 30. The bridging portion spaces at least a portion of the second side of the flexible seal 43 outwards from the perimeter or periphery of the mask body to which the clip is attached.

Figure 4A:
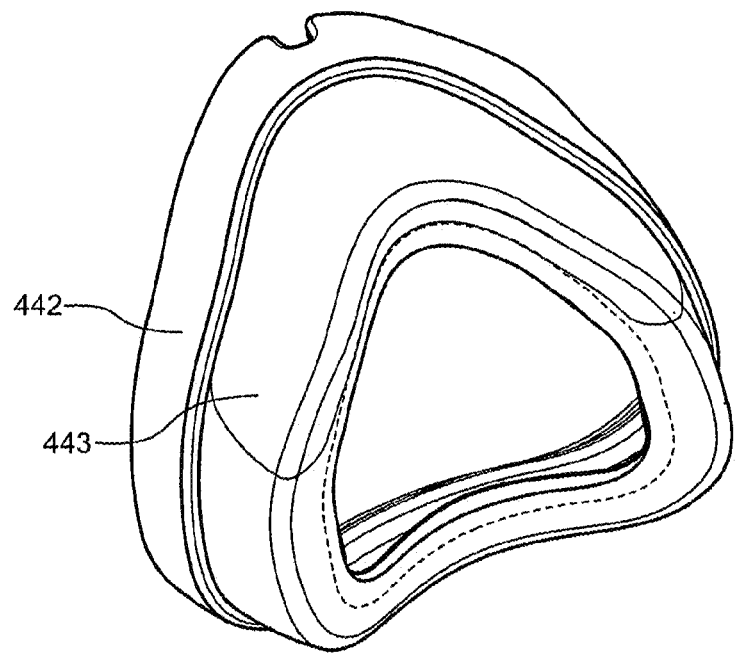
FIG. 4a is a perspective view of the mask seal assembly of the nasal mask of FIG. 1.
Figure 4B:
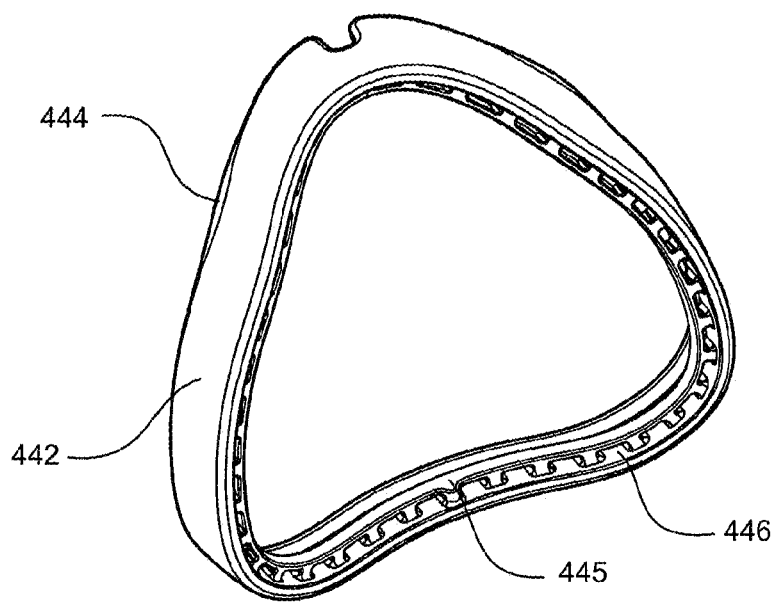
FIG. 4b is a perspective view of the seal clip of the mask seal assembly of the nasal mask of FIG. 1.
Figure 5:
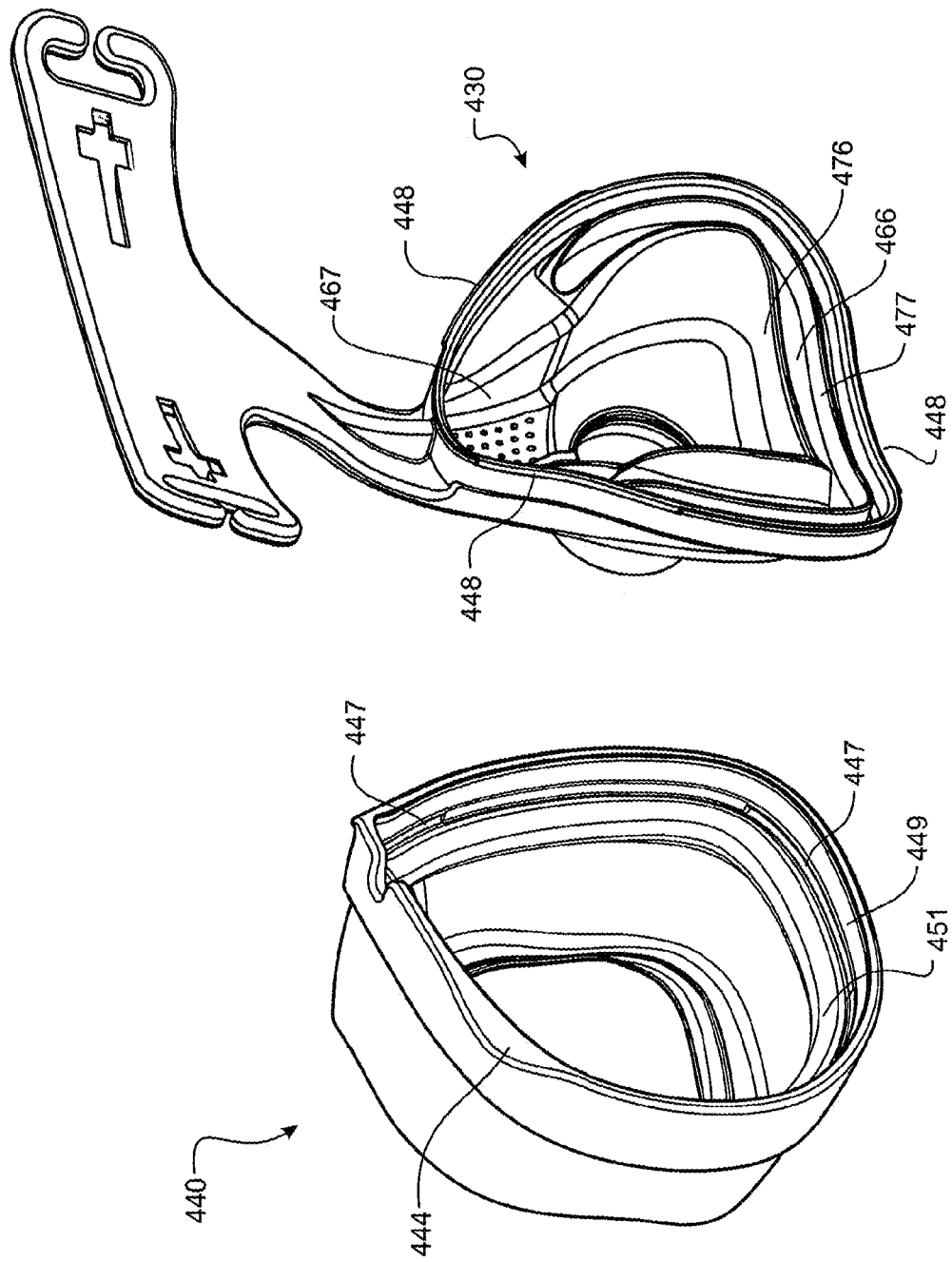
FIG. 5 is a perspective view showing the mask body and the mask seal assembly of the nasal mask of FIG. 1, with the mask seal assembly removed from the mask body.
Figure 6:
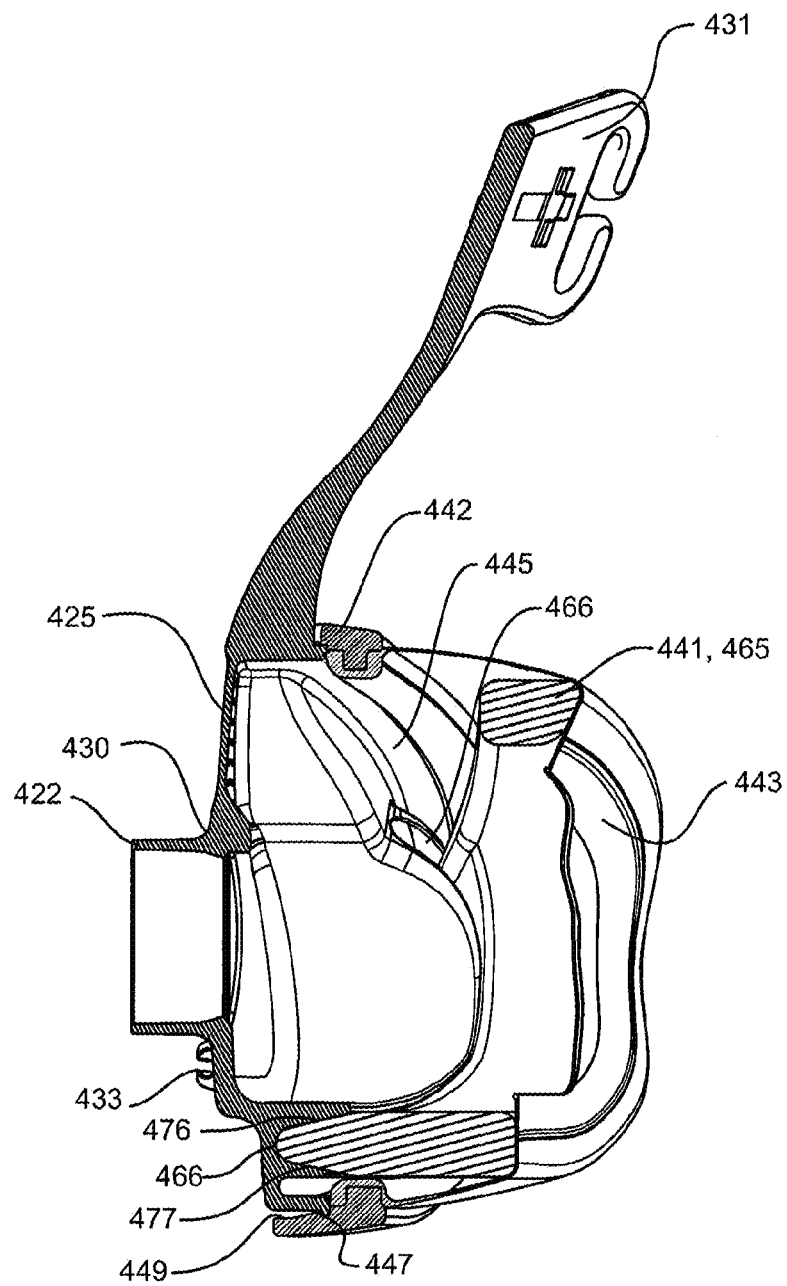
FIG. 6 is a sectional view on line X-X of the nasal mask of FIG. 2.

The mask body 30 may be used with a conventional seal assembly as disclosed in the prior art, for example as illustrated in FIG. 4A. Where a larger mask may be used by a larger user, the same mask body 30 useable with the conventional seal assembly may be used together with a seal assembly comprising a clip with a bridging portion 50. The bridging portion 50 allows a larger flexible seal 43 to be attached to the mask body 30, as illustrated in FIG. 8.

The present invention allows a single mask body 30 to be used for a range of differently sized users. For example, a range of differently sized seal assemblies may be provided. Each seal assembly may have a clip including a bridging portion 50. The bridging portion of each seal assembly may be a different size and each clip may be attached to a different size flexible seal. A smallest seal assembly in a range of differently sized seal assemblies may not include a bridging portion, the smallest seal assembly being a standard or conventional type seal assembly, for example as illustrated in FIG. 4A.

For supply to a user, a packaged interface product may include a single mask body, and a plurality of these seal assemblies, each of a different size with at least one of the seal assemblies having a bridging portion. The package may include instructions for selection and assembly of the seal assemblies to the mask body 30. The plurality of different size seal assemblies may be varied according to their size, by the size and arrangement of the bridging portion, the placement of an inner cushion and other aspects of variation described in this specification.

The range of seal assemblies for use with a single mask body preferably each have an identical or at least similar connection portion or side for attaching to the single mask body.

Figure 9A:
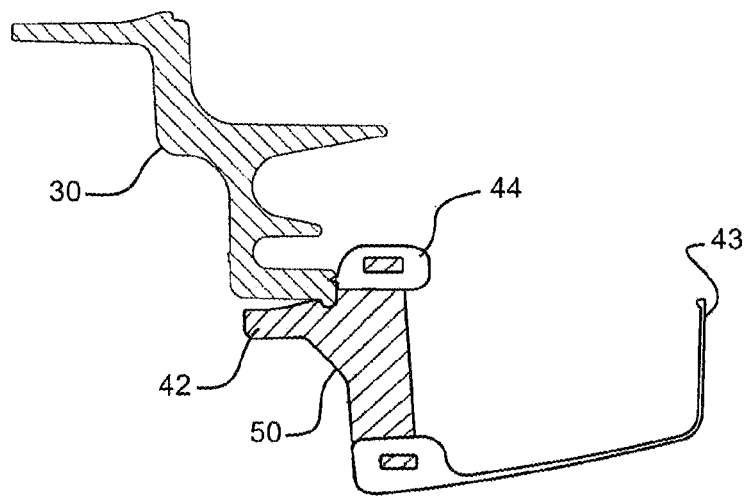
FIGS. 9A to 9C are part sectional views of a lower portion of a series of three differently sized mask assemblies.
Figure 9B:
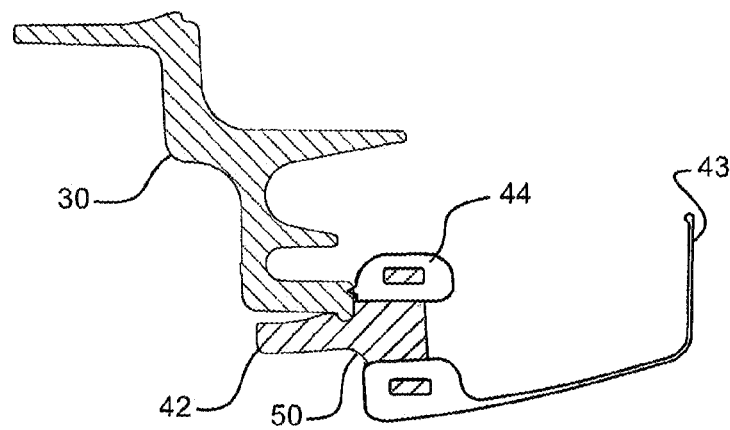
Figure 9C:
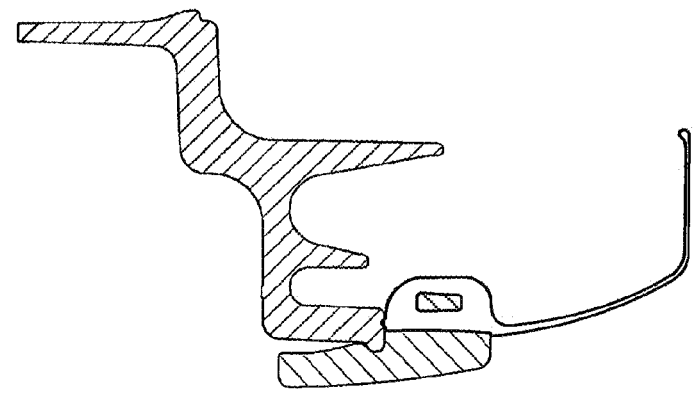

The clip with bridging portion expands a mask body to a larger size for use with a larger flexible seal. The mask body may be used with a first seal assembly comprising a flexible seal and clip without a bridging portion, for example as shown in FIG. 9C. The same mask body may be used with one or more seal assemblies each comprising a flexible seal and clip with a bridging portion to expand the mask body for use with a larger seal. A series of seal assemblies may be provided, each seal assembly in the series having a clip with a progressively larger bridging portion and corresponding larger flexible seal. A plurality of seal assemblies with clips each having differently sized bridging portions may be provided to achieve a range of mask assemblies, for appropriate selection by a user, as illustrated in FIGS. 9A and 9B.

As shown in FIG. 8, preferably the bridging portion of the clip has an outward dimension D that varies around the perimeter or periphery of the mask body. As shown in FIG. 8, preferably the outward dimension of the bridging portion is larger at a bottom portion of the clip and smaller at an upper portion of the clip. Alternatively, the bridging portion may have an outward dimension the same or similar around the periphery of the mask body.

The outward dimension of the bridging portion of a number of different seal assemblies may be the same in a particular portion of the mask body perimeter or periphery to which the clips are attached. For example, a range of different seal assemblies each may comprise a clip with bridging portion having a similar or the same outward dimension in the nasal bridge region, and each clip having a different outward dimension outside the nasal bridge region.

A mask according to the present invention may include a mask body having a forehead rest, for example as shown in FIG. 8. It can be advantageous for a mask having a forehead rest to have a range of different seal assemblies each comprising a clip with bridging portion having a similar or the same outward dimension in the nasal bridge region. With each clip in the range of seal assemblies having a similar outward dimension in the nasal bridge region, the distance between the top of the seal assembly and the forehead rest remains the same across the range of different sized seal assemblies. This is preferred as the distance the forehead rest is above the top of the mask body can be sized to be suitable for use with a range of different sized seal assemblies. By comparison, in a less preferred embodiment of the present invention, each seal assembly has a clip with bridging portion having a substantially constant outward dimension around the full parameter of the seal assembly. For larger seals, the distance between the top of the seal and the forehead rest therefore decreases.

The distance between the top of the seal and the forehead rest ideally should increase for increasing sized users. With each seal in a range of seals having the same bridging portion outward dimension in the nasal bridge region, the distance between the forehead rest and the top of each seal is the same, which is preferred to the previously described less preferred embodiment.

Preferably the clip has a bridging portion that tapers from a first outward dimension in a lower section of the seal to a second outward dimension in the nasal bridge region, the first dimension being greater than the second dimension.

The embodiment of FIG. 8 is illustrated without an inner cushion between the mask body 30 and the flexible seal 43. Preferably the mask assembly comprises an inner cushion between the mask body 30 and the flexible seal 43, or an inner cushion between the clip and the flexible seal.

Figure 10A:
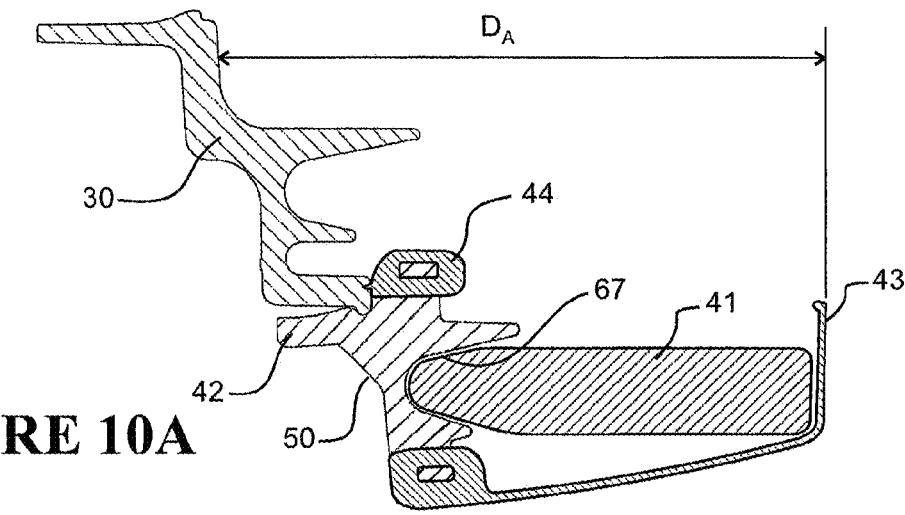
FIGS. 10A to 10C are part sectional views of a lower portion of three alternative mask assemblies each having a 'large' sized seal assembly.
Figure 10B:
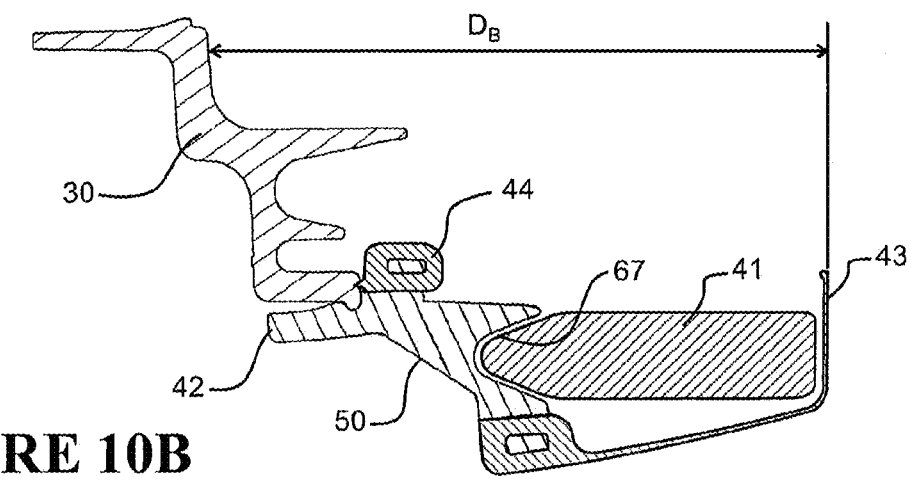
Figure 10C:
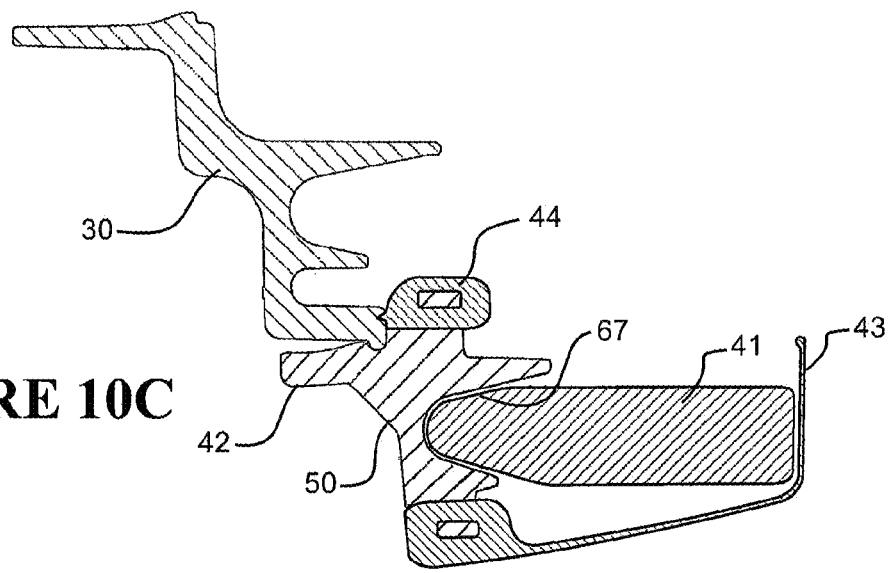

FIGS. 10A to 10C illustrate alternative clips with a bridging portion in the lower portion of the seal assembly for providing a 'large' sized seal 43 compared to other sealing assemblies. In each embodiment of FIGS. 10A to 10C, an inner cushion is located between the clip and the first side of the flexible seal 43. Preferably the inner cushion is located between the clip bridging portion and the first side of the flexible seal.

Preferably the bridging portion comprises a channel 67 for receiving and locating a side of the inner cushion at the clip. The channel may extend around a full circumference of the clip, or the channel may extend around a portion of a circumference of the clip. For example, the channel may extend around the clip outside the nasal bridge region only for use with a cushion having a raised nasal bridge region similar to the configuration of the inner cushion described in US2010/0006101.

In the embodiment of FIG. 10B, the bridging portion extends outwardly from the mask body 30 and also rearward, away from the general plane of the mask body, towards the user in use. The mask body and seal assembly combine to provide a cavity for surrounding the user's nose, or mouth or both. The rearward extension of the clip bridging portion increases the depth of the cavity provided by the mask assembly. For example, the depth $D_B$ of the cavity provided by the assembly of FIG. 10B with a rearward extension of the clip bridging portion is deeper than the depth $D_A$ of the cavity of the assembly of FIG. 10A with a clip bridging portion that does not extend rearward. The rearward extension of the bridging portion 50 of the embodiment of FIG. 10B spaces the second side of the seal 43 rearward from the perimeter or periphery of the mask body. For larger sized users, for example a user with a larger nose, a deeper internal cavity provided by the mask body and seal clip may reduce the likelihood of the user's nose touching an inside surface of the mask body compared to a mask assembly comprising a smaller seal 43. Extending the second side of the flexible seal 43 rearwards by providing a clip with a rearward extending bridging portion provides a deeper cavity to receive the user's nose compared to a mask assembly having a clip without a rearward extending bridging portion.

In the alternative embodiment of FIG. 10C, a deeper mask cavity is created compared to the embodiment of FIG. 10A by providing a deeper inner cushion and flexible seal for sealing against the user's face. The embodiments of FIGS. 10A and 10C each have the same shaped clip with bridging portion.

Figure 11A:
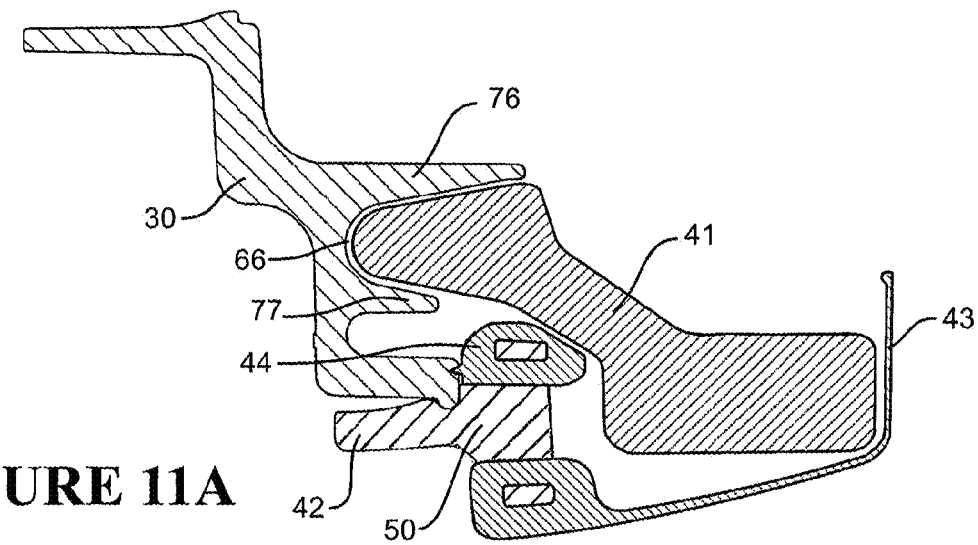
FIGS. 11A to 11C are part sectional views of a lower portion of three alternative mask assemblies each having a 'medium' sized seal assembly.
Figure 11B:
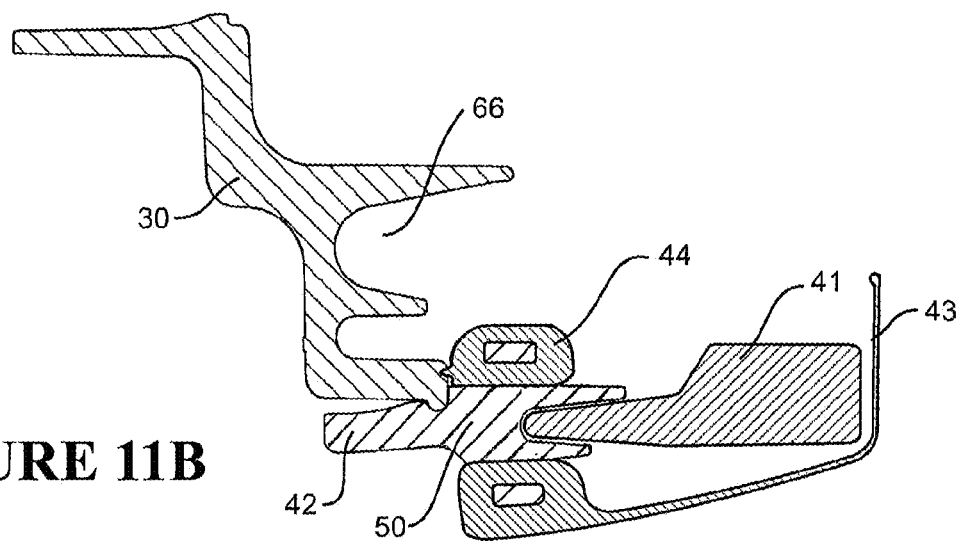
Figure 11C:
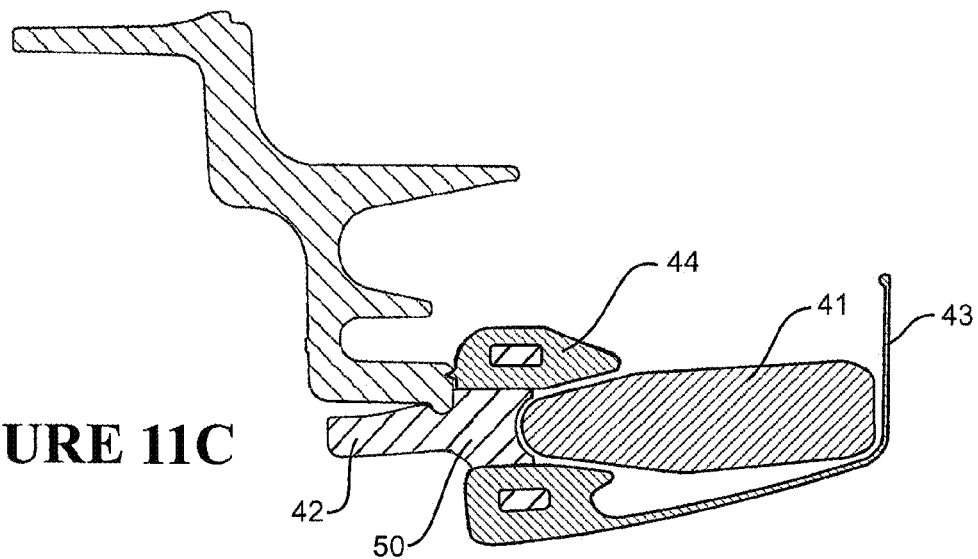

FIGS. 11A to 11C illustrate alternative clips with a bridging portion in the lower portion of the seal assembly for providing a 'medium' sized seal compared to other sealing assemblies. For example, the bridging portions 50 of the embodiments of FIGS. 11A to 11C have a smaller outward dimension compared to the bridging portions 50 of the embodiments of FIGS. 10A to 10C so that the seal 43 of the embodiments of FIGS. 11A to 11C are smaller than the seals of the embodiments of FIGS. 10A to 10C. And the bridging portions 50 of the embodiments of FIGS. 11A to 11C each provide a seal 43 that is larger than the seal of the illustrative embodiment comprising a clip with a bridging portion having a smaller outward dimension, or an embodiment comprising a clip without a bridging portion, for example the illustrative embodiment of FIG. 9C.

In the embodiment of FIG. 11A, an inner cushion 41 is located between the mask body 30 and the first side of the flexible seal 43, similar in concept to the aforementioned nasal mask illustrated in FIGS. 1-6. A channel 66 is formed in the mask body by two spaced apart members 76 and 77. A side of the inner cushion 41 in contact with the mask body is received in the channel 66.

FIGS. 11B and 11C illustrate embodiments similar to the embodiment of FIG. 10A described above, with the inner cushion located between the clip 42 and the flexible seal 43. However the outward dimension of the clip bridging portion of the 'medium' seal assemblies of FIGS. 11B and 11C is smaller than the outward dimension of the 'large' clip of the embodiment of FIG. 10A.

Due to the smaller bridging portion of the clip of the medium seal assembly of FIG. 11B, the side of the inner cushion in contact with the clip may be reduced in cross section compared to the inner cushion of the large seal assemblies of FIGS. 10A to 10C. In the alternative embodiment of FIG. 11C, a channel for receiving the cushion in the seal assembly is formed by material of the flexible seal that contacts a user's face in use, and material of a second flexible seal 44 on the other side of the bridging portion 50. The second flexible seal 44 is discussed below.

Figure 12:
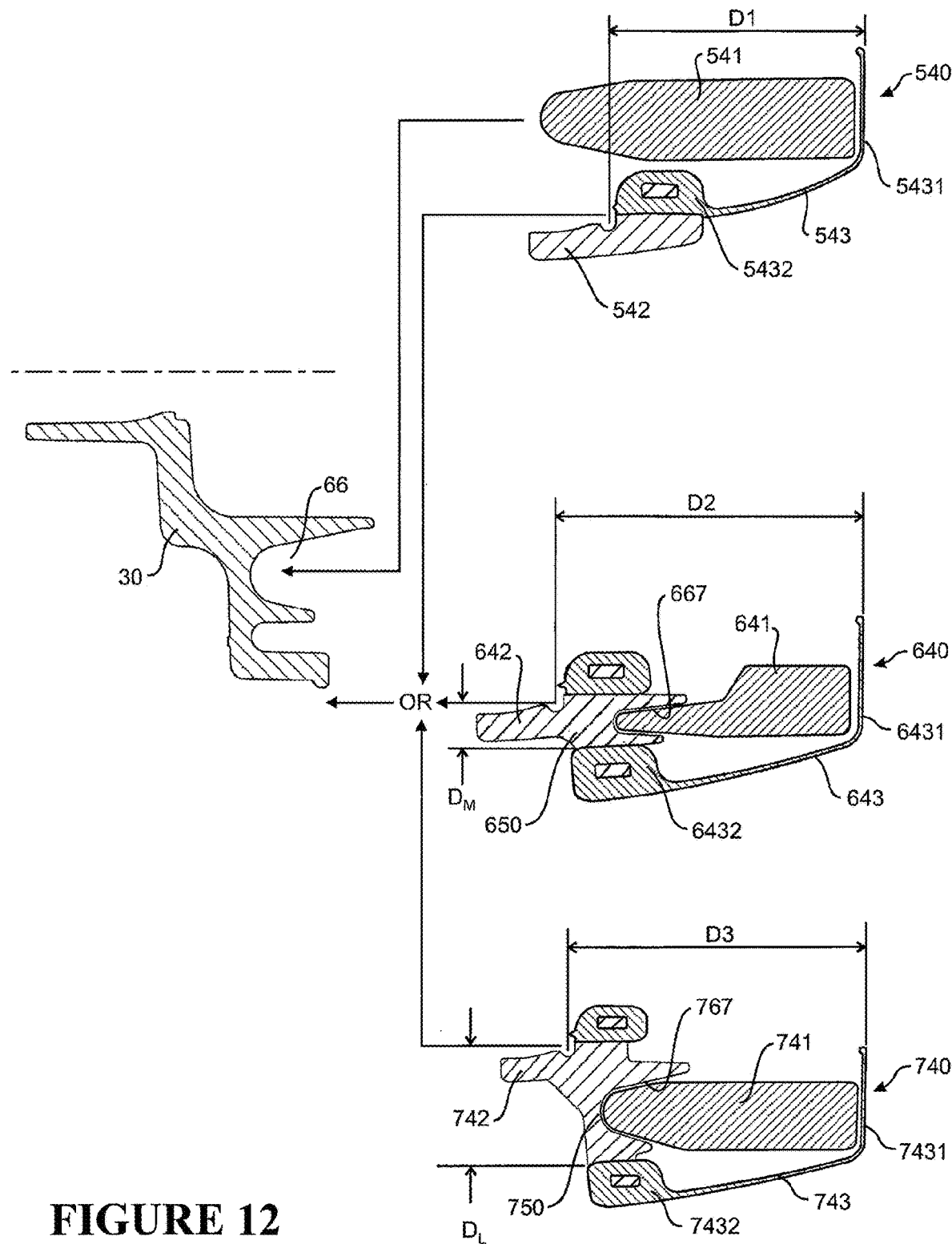
FIG. 12 is a diagram showing part sectional views of a common mask body and a range of mask seal assemblies for attachment to the common mask base.
Figure 13:
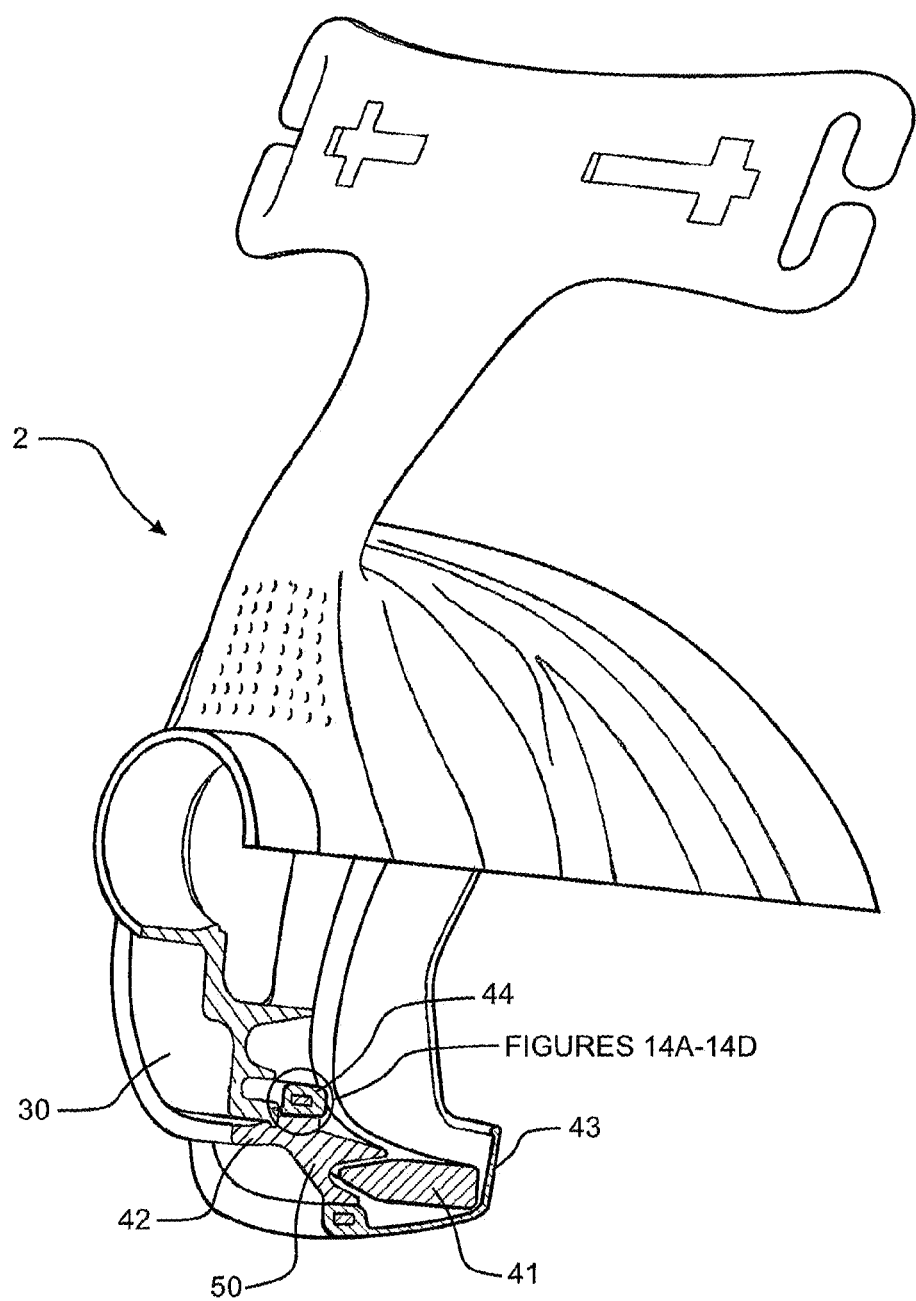
FIG. 13 is a perspective view of a mask assembly comprising the present invention with section cut away to show a lower portion of the mask assembly in cross section.

One embodiment of the present invention comprises a packaged mask assembly product including a single mask body and a plurality of seal assemblies of different sizes for use with the single mask body. For example, a mask package may include a single mask body 30 and a first seal assembly 540, a second seal assembly 640, and a third seal assembly 740, as shown in FIG. 12. The first seal assembly has a clip 542 and seal 543. The clip 542 does not have a bridging portion, the second side 5432 of the seal attached to the clip is not spaced outwards of the mask body when the seal assembly is attached to the mask body. For example, a portion of the material forming the seal 543 also forms a seal against the mask body. The mask assembly comprising the mask body 30 and the first seal assembly 540 may also include an inner cushion 541 located between the first side 5431 of the seal 542 and the mask body 30. The inner cushion is received in the channel 66 of the mask body 30. The mask assembly comprising the first seal assembly 540 is most suited to users with smaller facial features compared to other users.

Where the first seal assembly is not large enough for a particular user, that user may chose to use the second seal assembly 640. The second seal assembly has a clip 642 and seal 643. The clip 642 has a bridging portion 650 to space the second side 6432 of the seal attached to the clip outwards of the mask body when the seal assembly is attached to the mask body. The bridging portion has an outward dimension $D_m$ to space the second side of the seal outwards from the mask body by a distance. The bridging portion 650 of clip 642 allows a larger seal to be used with the body 30 by comparison with the seal of the first seal assembly 540. For example, the seal 643 attached to clip 642 of the second seal assembly 640 may be taller and wider in places compared to the seal 543 of the first seal assembly 540.

The mask assembly comprising the mask body 30 and the second seal assembly 640 may also include an inner cushion 641. In the illustrated example, the inner cushion 641 is located between the first side 6431 of the seal 643 and clip 642. The inner cushion 641 is received in the channel 667 of the clip 642.

Where the second seal assembly is not large enough for a particular user, that user may chose to use the third seal assembly 740. The third seal assembly has a clip 742 and seal 743. The clip 742 has a bridging portion 750 to space the second side 7432 of the seal attached to the clip outwards of the mask body when the seal assembly is attached to the mask body. The bridging portion has an outward dimension $D_L$ to space the second side of the seal outwards from the mask body by a distance. By comparison, the outward dimension of the bridging portion 750 of the third seal assembly 740 is larger than the outward dimension of the bridging portion 650 of the second seal assembly 640. The bridging portion 750 of clip 742 allows a larger seal to be used with the body 30 by comparison with the seal of the second seal assembly 640. For example, the seal 743 attached to clip 742 of the third seal assembly 740 may be taller and wider in places compared to the seal 743 of the second seal assembly.

The mask assembly comprising the mask body 30 and the third seal assembly 740 may also include an inner cushion 741. In the illustrated example, the inner cushion 741 is located between the first side 7431 of the seal 743 and clip 742. The inner cushion 741 is received in the channel 767 of the clip 742.

It can be seen from FIG. 12 that incorporating a bridging portion into the clip of a plurality of seal assemblies, each one with a different sized bridging portion, provides for a series of differently sized seal assemblies for use with a common mask body. A series of seal assemblies, each with a bridging portion with an increased outward dimension provides a series of increasing sized seal assemblies for use with a common mask body.

The seal of a seal assembly generally provides a flexible perimeter about the perimeter or periphery of the mask assembly. The seal surrounds an opening to the inside of the mask assembly. A second seal described as being larger than a first seal has a larger perimeter and opening than the first smaller seal. For example, the present invention may comprise a nasal mask package comprising a common mask body and a series of differently sized seal assemblies, each having a perimeter adapted to seal about a user's nose, the user's nose being received in an opening of the seal. Alternatively, the present invention may comprise a full face mask package comprising a common mask body and a series of differently sized seal assemblies, each having a perimeter adapted to seal about a user's nose and mouth, the user's nose and mouth being received in an opening of the seal.

Furthermore, a second seal described as being larger than a first seal not only has a larger perimeter and opening than the first smaller seal, but preferably also has a deeper seal assembly depth. The depth of a seal assembly is indicated in FIG. 12 by dimensions $D_1$, $D_2$ and $D_3$ for the three different sized seals illustrated. As shown, the depth of the seal assemblies increases for increasing seal sizes.

A large range of users can be accommodated by providing three different size mask seals for use with a common body. The three different size seals may conveniently be labeled as small, medium and large. A nasal mask suitable for a range of smaller users may have a seal height from the bridge of the nose to the philtrum area of around 45 mm. A nasal mask suitable for a range of medium sized users may have a seal height from the bridge of the nose to the philtrum area of around 54 mm. According to the present invention, the difference in height between the small seal and the medium seal is accommodated by the outward dimension of the bridging portion of the clip of the medium seal assembly. A nasal mask suitable for a range of larger sized users may have a seal height from the bridge of the nose to the philtrum area of around 58 mm. Similarly, according to the present invention, the difference in height between the small seal and the large seal is accommodated by the outward dimension of the bridging portion of the clip of the large seal assembly, the outward dimension of the bridging portion of the clip of the large seal assembly being greater than the outward dimension of the bridging portion of the clip of the medium seal assembly.

A series of differently sized seal assemblies may comprise a feature or features that are common to more than one seal assembly in the series. For example, a plurality of seal assemblies in a series of seal assemblies may each have the same or a similarly shaped nasal bridge region.

The present invention allows for a range of different types of seals to be used with a common mask body. For example, a common mask body may be used with a nasal seal assembly comprising a clip and seal for sealing around the nose of a user. The same mask body may also be used with a full face seal assembly comprising a clip and a seal for sealing around the nose and mouth of a user.

The seal of each seal assembly is attached to a first side of the seal assembly clip. A second side of the clip attaches to the common mask body. Each seal assembly clip has an identical or at least similar connection portion or second side for attaching to the common mask body. The clip of each seal assembly has a different first side to allow different types of seals to be used with the common mask body. The portion of the clip spanning between the first and second sides of the clip allows a different size or type of seal to be used with the common mask body. For example, the seal and first side of the clip of a full face seal assembly has a longer perimeter length than the seal and first side of the clip of a nasal seal assembly. The difference in perimeter lengths of the first sides of the clips of the full face and nasal seal assemblies is achieved by the clip of the full face seal assembly having bridging portion spanning between the first and second sides of the clip with a larger outward dimension than the clip of the nasal seal assembly. For example, the clip of the nasal seal assembly may have a bridging portion with a smaller outward dimension than the clip of the full face seal assembly, or the clip of the nasal seal assembly may not have a bridging portion, the second side of the seal of the nasal seal assembly not being spaced outwardly from the perimeter of the common mask body.

A range of different types of seals, each with a clip having a different first side allows many different types of seals to be used with a common mask body. For example the common mask body may be used with a cannula seal assembly, a nasal seal assembly, a mouth seal assembly and a full face assembly.

As described above, a sealing assembly according to one embodiment of the present invention comprises a rigid clip having a bridging portion for spacing the second side of the flexible seal in contact with a user's face outwards from the perimeter of the mask body. The flexible seal is attached to a first side of the clip. A second side of the clip attaches to the mask body. The bridging portion of the clip spans between the first and second sides of the clip.

Preferably the seal assembly further comprises a second flexible seal 44 attached to the second side of the clip for forming a seal between the seal assembly 40 and the mask body 30, as shown in FIGS. 10A to 14B. The bridging portion 50 spans between a first seal 43 for forming a seal against a user's face, and a second seal 44 for forming a seal between the seal assembly and the mask body 30.

Figure 15A:
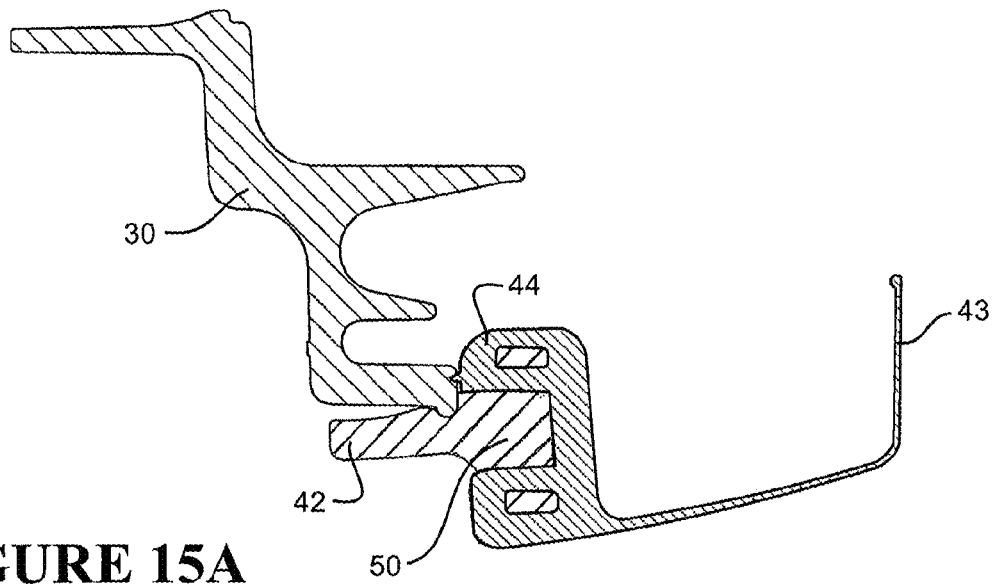
FIGS. 15A and 15B are part sectional views of a lower portion of two alternative mask assemblies each with a first seal and a second seal joined together across a bridging portion of a seal clip.
Figure 15B:
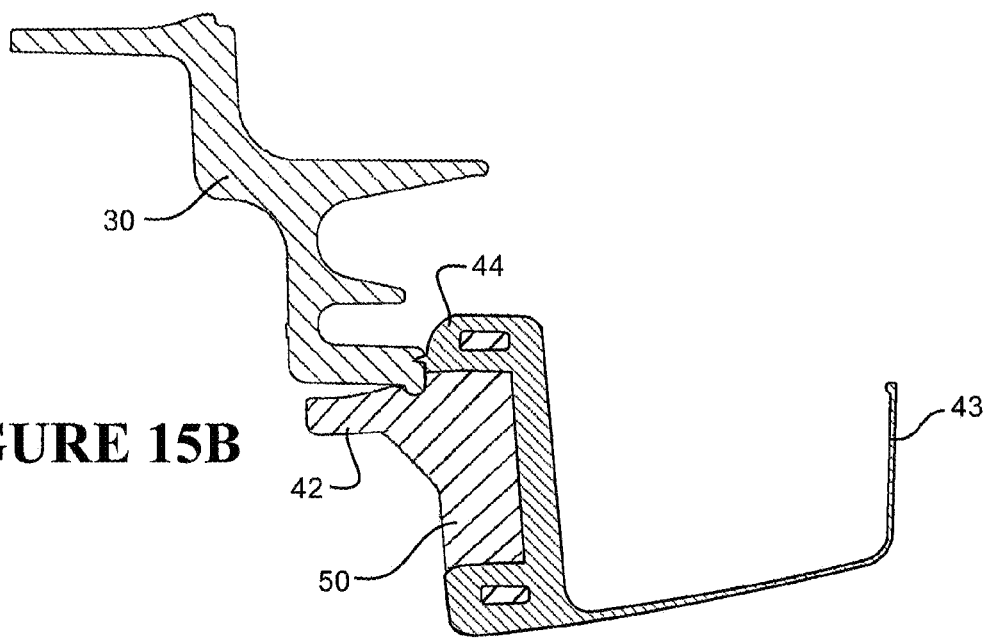

The first and second seals may be integrally formed, for example in an injection moulding process, the first and second seals integrally formed and joined together via a runner across or through the bridging portion. Alternatively, the first and second seals may be joined by overmoulding the seal material from the first flexible seal to the second flexible seal across the bridging portion as illustrated in FIGS. 15A and 15B. Alternatively, the first and second seals may be separately formed, for example by providing multiple insertion points, a multiple stage moulding process, or by a runner subsequently removed.

Figure 14A:
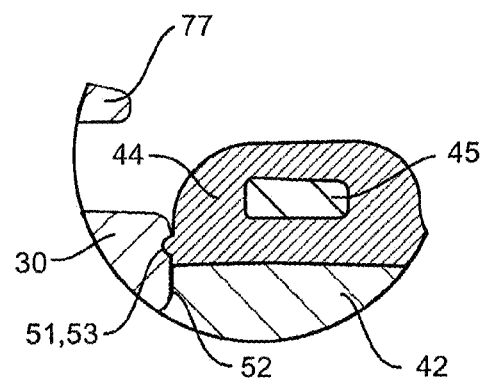
FIGS. 14A to 14D show cross sections of alternative seal arrangements for forming a seal between a seal assembly and a mask body of a mask assembly comprising the present invention.

Various second seal configurations for sealing between the seal assembly and the mask body are illustrated in FIGS. 14A to 14D. As illustrated in FIG. 14A, the second seal 44 has a bearing surface 51 extending around the perimeter of the clip. The second seal bearing surface 51 faces a corresponding bearing surface 52 on the mask body. The seal bearing surface and the mask bearing surface are in contact when the seal assembly is attached to the mask body in a butting engagement. When the seal assembly 40 is attached to the mask body 30, the second seal 44 at the bearing interface is compressed so that a sealing interface is formed between the seal assembly and the mask body.

Preferably, the clip has a raised ridge 45 running around the inside perimeter of the clip. The second seal 44 is compressed when the clip is attached to the mask body by being squashed between the raised ridge 45 and the mask body bearing surface 52 when the seal assembly 40 is attached to the mask body 30.

To assist with creating a good seal between the seal assembly and the mask body, a continuous rim 53 may be provided on the seal bearing surface 51. The rim provides a small contact area in contact with the mask body bearing surface 52. The small contact area allows a relatively high compression of the rim, and therefore effective seal, for a relatively small seal assembly to mask body engagement force.

Figure 14B:
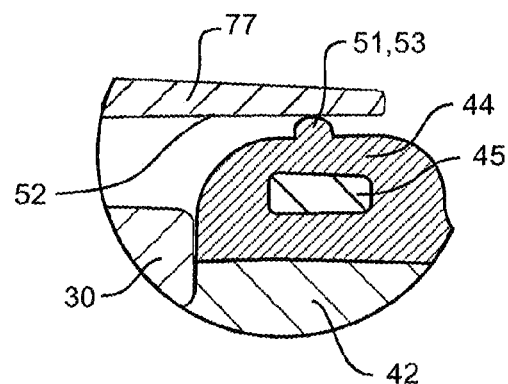

The alternative sealing arrangement illustrated in FIG. 14B comprises a seal that slides against a corresponding lateral member of the mask body during engagement of the seal assembly to the mask body. For example, a wall 77 forming a side of a channel 66 in the mask body for receiving the inner cushion as shown in FIG. 11A extends rearward to contact the second seal 44 when the seal assembly 40 is attached to the mask body 30. Preferably the second seal 44 comprises a raised rim 53 on the surface 51 that contacts the lateral member 77. The rim provides a small contact area in contact with the mask body bearing surface 52 in contact with the seal. The small contact area allows a relatively high compression of the rim, and therefore effective seal, for a relatively small seal assembly to mask body engagement force.

Figure 14C:
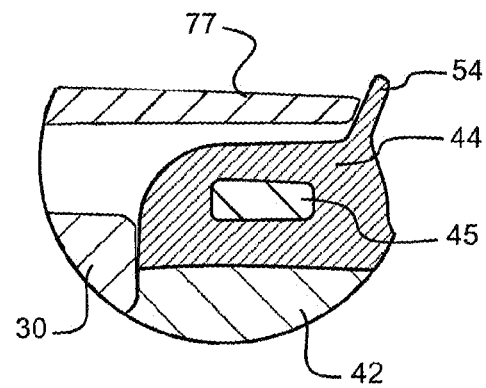

The alternative sealing arrangement illustrated in FIG. 14C comprises a lip 54 that bears against an end of a lateral member of the mask body 30. For example, a wall 77 forming a side of a channel 66 in the mask body for receiving the inner cushion as shown in FIG. 11A extends rearward to contact the lip 54 of the second seal 44 when the seal assembly 40 is attached to the mask body 30.

Figure 14D:
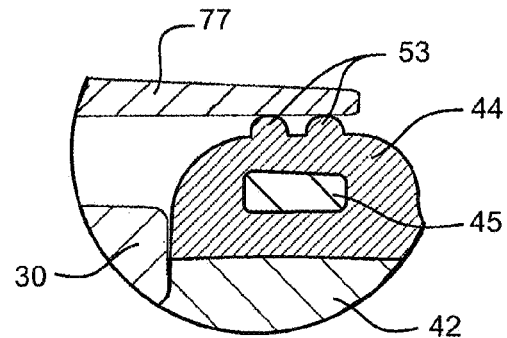

The alternative sealing arrangement illustrated in FIG. 14D is similar to the arrangement of FIG. 14B but includes two sealing rims 53 in sealing contact with a surface of the mask body.

The present invention has been described with reference to a nasal mask assembly. However, the present invention may equally be applied to other mask assemblies, for example full face masks that cover a user's nose and mouth.

Although certain preferred embodiments and examples have been discussed herein, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the present disclosure, including the appended claims.

We claim:

1. A mask seal assembly for use as part of an apparatus for supplying a flow of respiratory gases to a user, the mask seal assembly comprising:
a first seal and a second seal, each of flexible material, and a clip of rigid material,
the first seal having a first side and a second side, the first side of the first seal being shaped to approximately match contours of a face of the user and in use substantially seal against the face of the user, the second side attached to said clip,
the clip providing an interface extending substantially a full perimeter or periphery of the mask seal assembly, the clip having a first side and a second side, the second side of the first seal being attached to the first side of the clip, and the second side of the clip for releasably attaching the mask seal assembly to a mask body by way of direct engagement with the mask body,
the second seal attached to the second side of the clip for forming a seal between the mask seal assembly and the mask body,
wherein the clip comprises a bridging portion spanning between the first side and the second side of the clip to space at least a portion of the second side of the first seal outwards from a perimeter or periphery of the second side of the clip,
wherein the first seal and the second seal are integrally formed and joined together across the bridging portion via a runner across or through the bridging portion.

2. The mask seal assembly of claim 1, wherein the first seal and the second seal are joined by overmoulding the flexible material of the first seal to the second seal across the bridging portion.

3. The mask seal assembly of claim 1, wherein the first seal and the second seal are separately formed by:
providing multiple insertion points,
a multiple stage moulding process, or
a second runner which is subsequently removed.

4. The mask seal assembly of claim 1, wherein the second seal comprises a lip.

5. The mask seal assembly of claim 4, wherein the lip is configured to bear against an end of a lateral member of the mask body.

6. The mask seal assembly of claim 1, wherein the bridging portion has an outward dimension (D) that is approximately the same around the perimeter or periphery of the mask seal assembly.

7. The mask seal assembly of claim 1, wherein the bridging portion has an outward dimension (D) that varies around the perimeter or periphery of the second side of the clip.

8. The mask seal assembly of claim 1, wherein the bridging portion extends rearward away from a front of the mask body to which the mask seal assembly is configured to be attached to in use and towards the face of the user in use.

9. The mask seal assembly of claim 1, wherein the mask seal assembly is adapted to releasably attach to a rear perimeter of the mask body defining a hollow space for receiving or covering a nose or a mouth of the user, or both, and having an inlet through which the flow of respiratory gases is provided to an interior of the mask body.

10. The mask seal assembly of claim 1, wherein the clip is manufactured from polycarbonate, ABS, nylon, acetyl or other similar rigid plastic, and the first seal is formed from silicone with a Shore-A hardness of less than 60.

11. A mask assembly for supplying a flow of respiratory gases to a user, the mask assembly comprising:
a mask seal assembly according to claim 1, and
the mask body.

12. The mask assembly of claim 11, wherein the mask body includes an inlet for receiving a flow of gases into the mask assembly.

13. A packaged interface product comprising:
a single mask body, and
a plurality of mask seal assemblies each of a different size and comprising a connection portion or side configured to attach to the single mask body,
wherein at least one of the plurality of mask seal assemblies is as claimed in claim 1.

14. The packaged interface product of claim 13, wherein:
two or more of the plurality of mask seal assemblies are as claimed in claim 1, and
an outward dimension (D) of the bridging portion of each of the two or more of the plurality of mask seal assemblies are the same in a particular portion of the mask body perimeter or periphery to which the clips are attached.

15. A mask seal assembly for use as part of an apparatus for supplying a flow of respiratory gases to a user, the mask seal assembly comprising:
a first seal and a second seal, each of flexible material, and a clip of rigid material, the first seal having a first side and a second side, the first side of the first seal being shaped to approximately match contours of a face of the user and in use substantially seal against the face of the user, the second side attached to said clip, the clip providing an interface extending substantially a full perimeter or periphery of the mask seal assembly, the clip having a first side and a second side, the second side of the first seal being attached to the first side of the clip, and the second side of the clip for releasably attaching the mask seal assembly to a mask body, the second seal attached to the second side of the clip for forming a seal between the mask seal assembly and the mask body, wherein the clip comprises a bridging portion spanning between the first side and the second side of the clip to space at least a portion of the second side of the first seal outwards from a perimeter or periphery of the second side of the clip, wherein the first seal and the second seal are integrally formed and joined together across the bridging portion via a runner across or through the bridging portion, wherein the bridging portion spaces the second side of the first seal outwards from the perimeter or periphery of the second side of the clip by at least 10 mm.

16. A packaged interface product comprising:
a single mask body, and
a plurality of mask seal assemblies each of a different size and comprising a connection portion or side configured to attach to the single mask body, wherein at least one of the plurality of mask seal assemblies comprises:
a first seal and a second seal, each of flexible material, and
a clip of rigid material,
the first seal having a first side and a second side, the first side of the first seal being shaped to approximately match contours of a face of the user and in use substantially seal against the face of the user, the second side attached to said clip,
the clip providing an interface extending substantially a full perimeter or periphery of the mask seal assembly, the clip having a first side and a second side, the second side of the first seal being attached to the first side of the clip, and the second side of the clip for releasably attaching the mask seal assembly to a mask body,
the second seal attached to the second side of the clip for forming a seal between the mask seal assembly and the mask body,
wherein the clip comprises a bridging portion spanning between the first side and the second side of the clip to space at least a portion of the second side of the first seal outwards from a perimeter or periphery of the second side of the clip,
wherein the first seal and the second seal are integrally formed and joined together across the bridging portion via a runner across or through the bridging portion,
wherein the bridging portion and the first seal is one of a series of sizes, each one of the series of sizes suitable for sealing against a differently sized user's face.

17. A mask seal assembly for use as part of an apparatus for supplying a flow of respiratory gases to a user, the mask seal assembly comprising:
a clip of rigid material providing an interface extending substantially a full perimeter or periphery of the mask seal assembly, the clip comprising:
a first side;
a second side including a connection portion configured to releasably engage the mask seal assembly to a mask body assembly; and
a bridging portion spanning between the first side and the second side of the clip;
a first seal of flexible material, the first seal having a first side and a second side, the first side of the first seal being shaped to approximately match contours of a face of the user and in use substantially seal against the face of the user, the second side of the first seal being attached to the first side of the clip;
a second seal of flexible material, the second seal attached to the second side of the clip, wherein the first seal and the second seal are integrally formed and joined together across the bridging portion via a runner across or through the bridging portion;
wherein the bridging portion spaces at least a portion of the second side of the first seal outwards from a perimeter or periphery of the second side of the clip.

18. The mask seal assembly of claim 17, wherein the first seal and the second seal are joined by overmoulding the flexible material of the first seal to the second seal across the bridging portion.

19. The mask seal assembly of claim 17, wherein the second seal comprises a lip.

20. The mask seal assembly of claim 19, wherein the lip is configured to bear against an end of a lateral member of the mask body assembly.

21. The mask seal assembly of claim 17, wherein the bridging portion has an outward dimension (D) that varies around the perimeter or periphery of the second side of the clip.

22. The mask seal assembly of claim 17, wherein the bridging portion extends rearward away from a front of the mask body assembly to which the mask seal assembly is configured to be attached to in use and towards the face of the user, in use.

23. The mask seal assembly of claim 17, wherein the mask seal assembly is adapted to releasably attach to a rear perimeter of the mask body assembly defining a hollow space for receiving or covering a nose or a mouth of the user, or both, and having an inlet through which the flow of respiratory gases is provided to an interior of the mask body assembly.

24. The mask seal assembly of claim 17, in combination with the mask body assembly, the mask body assembly comprising an inlet configured to connect with a respiratory gas supply.

25. A mask assembly for supplying a flow of respiratory gases to a user, the mask assembly comprising:
the mask seal assembly according to claim 17, and the mask body assembly.

\* \* \* \* \*